(12) United States Patent
Zumbrum et al.

(10) Patent No.: US 11,027,108 B2
(45) Date of Patent: Jun. 8, 2021

(54) FLUID TRANSFER ASSEMBLY WITH A JUNCTION HAVING MULTIPLE FLUID PATHWAYS

(71) Applicant: Sartorius Stedim North America Inc., Bohemia, NY (US)

(72) Inventors: Michael A. Zumbrum, New Oxford, PA (US); Kevin Perdue, New Oxford, PA (US)

(73) Assignee: Sartorius Stedim North America Inc., Bohemia, NY (US)

( * ) Notice: Subject to any disclaimer, the term of this patent is extended or adjusted under 35 U.S.C. 154(b) by 63 days.

(21) Appl. No.: 16/189,898

(22) Filed: Nov. 13, 2018

(65) Prior Publication Data

US 2019/0143093 A1 May 16, 2019

Related U.S. Application Data

(60) Provisional application No. 62/585,699, filed on Nov. 14, 2017.

(51) Int. Cl.
*A61M 39/10* (2006.01)
*B29C 65/00* (2006.01)
(Continued)

(52) U.S. Cl.
CPC .......... *A61M 39/08* (2013.01); *A61M 39/105* (2013.01); *A61M 39/146* (2013.01);
(Continued)

(58) Field of Classification Search
CPC .. A61M 39/08; A61M 39/105; A61M 39/146; A61M 2039/1077;
(Continued)

(56) References Cited

U.S. PATENT DOCUMENTS

| 4,581,012 A | 4/1986 | Brown et al. |
| 4,676,898 A | 6/1987 | Saxena |

(Continued)

FOREIGN PATENT DOCUMENTS

| CN | 102218226 | 10/2011 |
| DE | 102014104334 | 10/2015 |

(Continued)

OTHER PUBLICATIONS

International Search Report and the Written Opinion of the International Searching Authority for PCT/US2018/060828; dated Feb. 1, 2019.

(Continued)

*Primary Examiner* — Jason K Niesz
(74) *Attorney, Agent, or Firm* — Womble Bond Dickinson (US) LLP

(57) ABSTRACT

A fluid transfer assembly is described. The fluid transfer assembly includes a unitary junction having an upstream portion and a downstream portion, the unitary junction defining a plurality of curved fluid pathways between the upstream portion and the downstream portion. The assembly also includes at least one flexible fluid conduit sealed to the junction in fluid communication with at least one of the plurality of curved fluid pathways.

35 Claims, 38 Drawing Sheets

(51) Int. Cl.
*A61M 39/08* (2006.01)
*A61M 39/14* (2006.01)
*B29C 57/10* (2006.01)
*B33Y 10/00* (2015.01)
*B33Y 30/00* (2015.01)

(52) U.S. Cl.
CPC ........ *B29C 57/10* (2013.01); *B29C 66/73921* (2013.01); *A61M 2039/1077* (2013.01); *B29C 2793/009* (2013.01); *B33Y 10/00* (2014.12); *B33Y 30/00* (2014.12)

(58) Field of Classification Search
CPC .............. B29C 66/73921; B29C 57/10; B29C 2793/009; B33Y 30/00; B33Y 10/00
See application file for complete search history.

(56) References Cited

U.S. PATENT DOCUMENTS

| | | |
|---|---|---|
| 4,701,159 A | 10/1987 | Brown et al. |
| 5,052,105 A | 10/1991 | Mische et al. |
| D324,568 S | 3/1992 | Marken |
| 5,197,895 A | 3/1993 | Stupecky |
| 5,219,185 A | 6/1993 | Oddenino |
| 5,476,116 A | 12/1995 | Price et al. |
| 5,478,119 A | 12/1995 | Dye |
| 6,179,823 B1 | 1/2001 | Niedospial |
| 6,610,200 B1 | 8/2003 | Leijon et al. |
| 6,733,730 B1 | 5/2004 | Griffiths et al. |
| 6,905,595 B2 | 6/2005 | Gebauer |
| 7,563,243 B2 | 7/2009 | Mendels |
| 7,931,859 B2 | 4/2011 | Mlodzinski et al. |
| 8,025,271 B2 | 9/2011 | Kolodner et al. |
| 8,092,409 B2 | 1/2012 | Mros et al. |
| 8,196,614 B2 | 6/2012 | Kriheli |
| 8,281,807 B2 | 10/2012 | Trombley et al. |
| 8,336,313 B2 | 12/2012 | McMasters et al. |
| 8,372,058 B2 | 2/2013 | Schilp et al. |
| 8,505,396 B2 | 8/2013 | Zumbrum |
| 8,505,586 B2 | 8/2013 | Zumbrum |
| 8,562,572 B2 | 10/2013 | Proulx et al. |
| 8,690,120 B2 | 4/2014 | Hartnett et al. |
| 8,865,427 B2 | 10/2014 | Poo et al. |
| 9,095,693 B2 | 8/2015 | Buisson |
| 9,211,364 B2 | 12/2015 | Croizat et al. |
| 9,227,046 B1 | 1/2016 | Douglas |
| 9,358,333 B2 | 6/2016 | Trombley, III et al. |
| 9,376,224 B2 | 6/2016 | Gonnelli et al. |
| 9,376,305 B2 | 6/2016 | Zumbrum |
| 9,526,886 B2 | 12/2016 | Mastri et al. |
| 9,528,632 B2 | 12/2016 | Glaun |
| 9,597,732 B2 | 3/2017 | Lewis et al. |
| 9,675,520 B2 | 6/2017 | Rogers et al. |
| 9,700,844 B2 | 7/2017 | Schick |
| 9,706,793 B2 | 7/2017 | Hayakawa |
| 9,726,314 B2 | 8/2017 | Py |
| 9,771,629 B2 | 9/2017 | Soloway |
| 9,784,111 B2 | 10/2017 | Luo et al. |
| 9,802,172 B2 | 10/2017 | Janders et al. |
| 9,857,002 B2 | 1/2018 | Ott et al. |
| 9,901,729 B2 | 2/2018 | Vigna et al. |
| 9,907,728 B2 | 3/2018 | Kyle et al. |
| 9,926,185 B2 | 3/2018 | Davis et al. |
| 9,938,128 B2 | 4/2018 | Py et al. |
| 9,944,510 B2 | 4/2018 | Zumbrum |
| 9,975,753 B1 | 5/2018 | Zumbrum et al. |
| 9,987,508 B2 | 6/2018 | Cockerham et al. |
| 10,006,567 B2 | 6/2018 | Zumbrum |
| 2004/0099154 A1 | 5/2004 | Raschle |
| 2005/0124935 A1* | 6/2005 | McMichael ......... A61J 15/0065 604/129 |
| 2005/0132821 A1 | 6/2005 | Furey |
| 2005/0256461 A1* | 11/2005 | DiFiore ............... A61M 39/105 604/247 |
| 2010/0123094 A1 | 5/2010 | Zumbrum |
| 2010/0154569 A1 | 6/2010 | Guedon |
| 2010/0158759 A1 | 6/2010 | Olivier |
| 2010/0318069 A1 | 12/2010 | Hall et al. |
| 2011/0121558 A1 | 5/2011 | Kanner |
| 2011/0155258 A1 | 6/2011 | Zumbrum |
| 2012/0074051 A1 | 3/2012 | Gebauer et al. |
| 2013/0304039 A1* | 11/2013 | Chung ................. A61M 39/105 604/537 |
| 2014/0074015 A1* | 3/2014 | Mastri ................ A61B 17/3417 604/26 |
| 2014/0076454 A1 | 3/2014 | Kjar |
| 2014/0137519 A1 | 5/2014 | Goodwin et al. |
| 2014/0191501 A1 | 7/2014 | Brugger et al. |
| 2014/0353878 A1 | 12/2014 | Driessen et al. |
| 2015/0080814 A1 | 3/2015 | Lambert et al. |
| 2016/0195208 A1 | 7/2016 | Cassiday et al. |
| 2016/0199914 A1 | 7/2016 | Potter |
| 2016/0202101 A1 | 7/2016 | Sparks et al. |
| 2016/0238324 A1 | 8/2016 | Butcher et al. |
| 2016/0361488 A1* | 12/2016 | Perrenoud ............... A61M 5/38 |
| 2017/0021355 A1 | 1/2017 | Olivier et al. |
| 2017/0102089 A1 | 4/2017 | Griffin, Jr. et al. |
| 2017/0167652 A1 | 6/2017 | Snyder et al. |
| 2017/0173495 A1 | 6/2017 | Valery et al. |
| 2017/0204989 A1 | 7/2017 | Burkhart et al. |
| 2017/0219134 A1 | 8/2017 | Kedor et al. |
| 2017/0239141 A1 | 8/2017 | Davis et al. |
| 2017/0306766 A1 | 10/2017 | Munzer |
| 2018/0163898 A1 | 6/2018 | Von Arb |

FOREIGN PATENT DOCUMENTS

| | | |
|---|---|---|
| EP | 2802415 | 11/2014 |
| EP | 2805737 | 11/2014 |
| EP | 2144589 | 7/2016 |
| EP | 3206816 | 8/2017 |
| EP | 3215286 | 9/2017 |
| WO | 1998054568 | 12/1998 |
| WO | 2013072348 | 5/2013 |
| WO | 2017063623 | 4/2017 |
| WO | 2017082895 | 5/2017 |
| WO | 2017156240 | 9/2017 |
| WO | 2018117949 | 6/2018 |

OTHER PUBLICATIONS

International Search Report and the Written Opinion of the International Searching Authority for PCT/US2019/061229; dated Jan. 29, 2020.

* cited by examiner

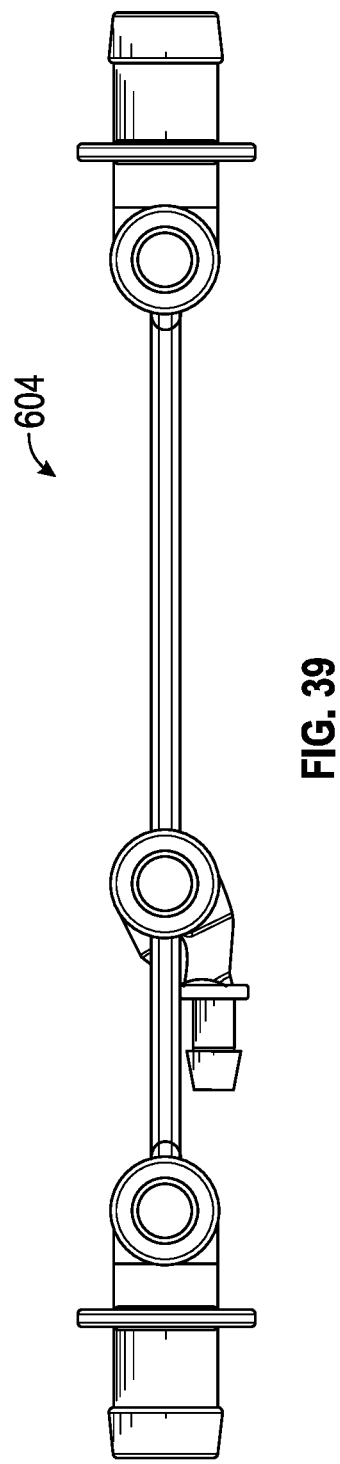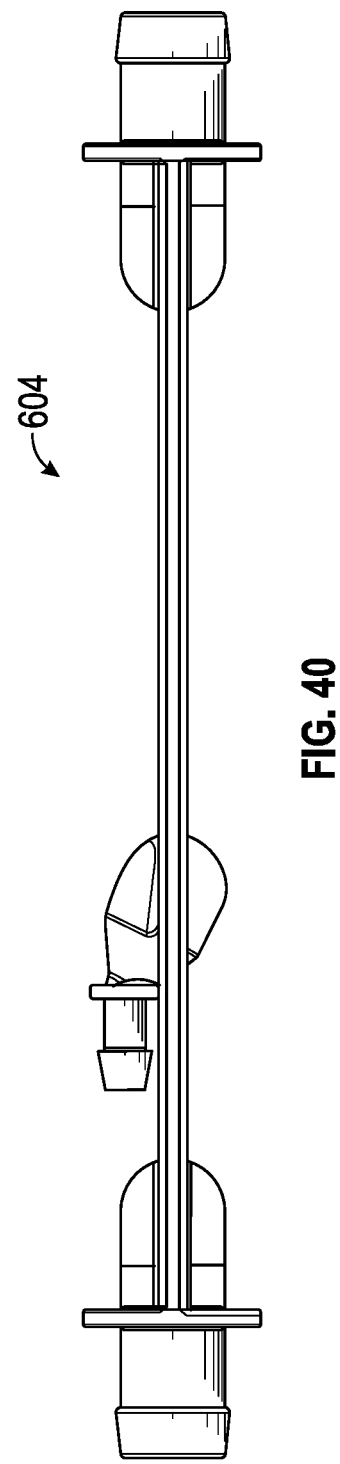

FLUID TRANSFER ASSEMBLY WITH A JUNCTION HAVING MULTIPLE FLUID PATHWAYS

CROSS REFERENCE TO RELATED APPLICATIONS

This application claims the benefit of U.S. Provisional Patent Application No. 62/585,699, filed Nov. 14, 2017.

INCORPORATION BY REFERENCE

U.S. Provisional Patent Application No. 62/585,699, which was filed Nov. 14, 2017, is hereby incorporated by reference for all purposes as if presented herein in its entirety.

TECHNICAL FIELD

This disclosure relates generally to junctions allowing for the transfer of fluids, particularly liquids, mixtures, or suspensions, from a source to a destination through at least one flexible conduit. The disclosure is particularly related to assemblies with a junction for use in aseptic systems.

BACKGROUND

Biopharmaceutical and pharmaceutical drug developers and manufactures often develop and manufacture products in a fluid form. These products must be handled with care to maintain an aseptic environment and avoid contamination. Drugs developed and produced by biopharmaceutical and pharmaceutical companies are often produced through a multitude of steps that may require transfer of the fluids through conduits for purposes of sampling, packaging, mixing, separating, or passing between stations for various steps of the manufacturing process.

The manufacturing and testing processes required by biopharmaceutical and pharmaceutical companies require significant opportunities for fluid transfer. Each occurrence of fluid transfer that relies upon separate containers, conduits, or components to leave the source and arrive at the destination creates an opportunity for leaks to occur or contamination to enter.

Often, several fluid pathways are required to enter or exit various containers. Traditionally, the fluid pathways have all been maintained independent of one another, requiring a large number of separate fittings between conduits and requiring a significant amount of space to accommodate the fittings for each fluid pathway separately.

The present disclosure describes improvements to maintain aseptic environments and avoid contamination during fluid transfer by minimizing leak points, increasing organization of fluid pathways, reducing space requirements and simplifying assembly to produce a reliable low-cost fluid transfer assembly. Because fluid transfer assemblies are often rendered aseptic and are intended for a single use, maintaining a low cost through reducing assembly steps can provide significant advantages.

SUMMARY

An embodiment of the present disclosure includes a fluid transfer assembly comprising a unitary junction having an upstream portion and a downstream portion, the unitary junction defining a plurality of curved fluid pathways between the upstream portion and the downstream portion. The assembly further comprises at least one flexible fluid conduit sealed to the junction in fluid communication with at least one of the plurality of curved fluid pathways.

Another embodiment of the present disclosure includes a fluid transfer assembly comprising a unitary junction having an upstream portion and a downstream portion, the unitary junction defining a plurality of curved fluid pathways between the upstream portion and the downstream portion. The assembly also includes at least one flexible fluid conduit connected (e.g., sealed) to the junction in fluid communication with at least one of the plurality of curved fluid pathways. At least one of the upstream portion and the downstream portion comprises a plurality of male inserts respectively corresponding with the plurality of fluid pathways, the plurality of male inserts are configured for insertion into the at least one fluid conduit to facilitate fluid communication. The unitary junction is formed from a plurality of layers of material, each layer being approximately the same thickness.

A further embodiment of the present disclosure includes a method of manufacturing a fluid transfer assembly. The method comprises forming sequential layers of material using an additive manufacturing device to form a unitary junction having an upstream portion and a downstream portion, the unitary junction defining a plurality of curved fluid pathways between the upstream portion and the downstream portion. At least one of the upstream portion and the downstream portion comprises a plurality of male inserts respectively corresponding with the plurality of fluid pathways. The method also includes inserting at least one of the plurality of male inserts into a lumen of a flexible fluid conduit and securing the flexible fluid conduit to the junction.

These and other aspects of the present disclosure will become apparent to those skilled in the art after a reading of the following description of the preferred embodiments, when considered in conjunction with the drawings. It should be understood that both the foregoing general description and the following detailed description are explanatory only and are not restrictive of the invention as claimed.

BRIEF DESCRIPTION OF THE DRAWINGS

FIGS. 37, 38, 39, 40, 41, 42, and 43 illustrate several views of a junction according to yet another embodiment that is suitable for use in a fluid transfer assembly according to embodiments of the present disclosure.

DETAILED DESCRIPTION

Exemplary embodiments of this disclosure are described below and illustrated in the accompanying figures, in which like numerals refer to like parts throughout the several views. The embodiments described provide examples and should not be interpreted as limiting the scope of the invention. Other embodiments, and modifications and improvements of the described embodiments, will occur to those skilled in the art and all such other embodiments, modifications and improvements are within the scope of the present invention. Features from one embodiment or aspect may be combined with features from any other embodiment or aspect in any appropriate combination. For example, any individual or collective features of method aspects or embodiments may be applied to apparatus, product or component aspects or embodiments and vice versa.

Figure 1:
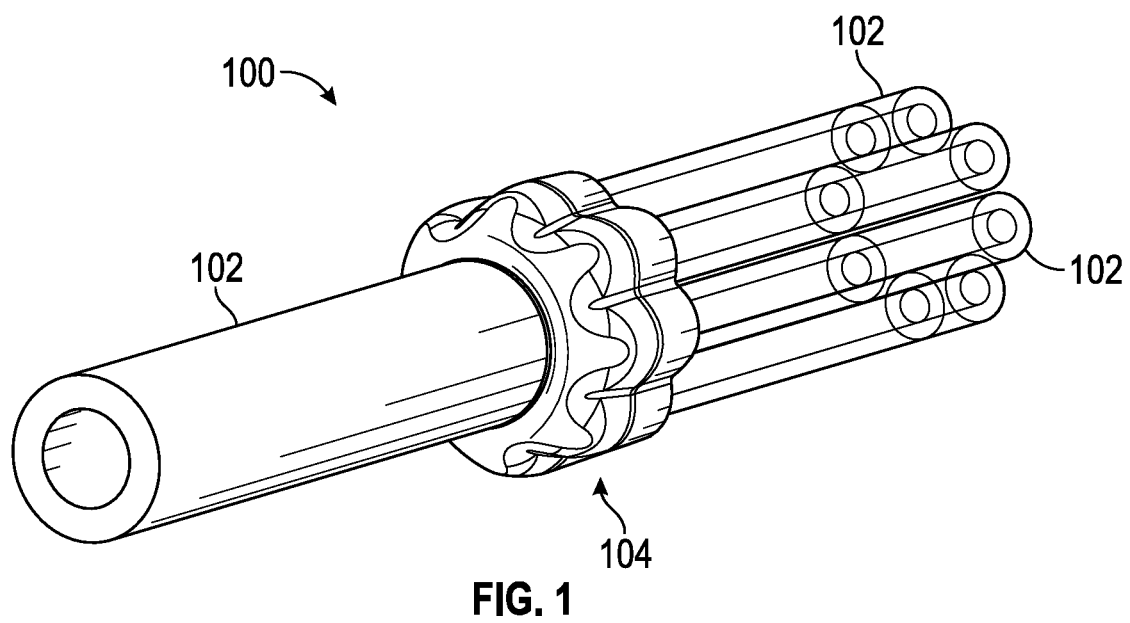
FIG. 1 illustrates a fluid transfer assembly according to a first embodiment.

FIG. 1 is a fluid transfer assembly 100 that may be suitable for use in conveying liquids, mixtures, or suspensions during the manufacture of biopharmaceutical and pharmaceutical products in an aseptic manner. The fluid transfer assembly 100 is intended to provide aseptic fluid transfer paths. The fluid transfer assembly 100 is not particularly limited to use in pharmaceutical development or manufacturing.

The fluid transfer assembly 100 is shown with a number of fluid conduits 102 attached to a junction 104. In the illustrated embodiment, fluid conduits 102 are attached to both the upstream and downstream portions of the junction 104. In other embodiments, one of the upstream or downstream portions of the junction 104 may be attached to vessels or other containers.

As used herein, the terms upstream and downstream are used for clarity of the description to refer to the optional direction of flow of fluid through the junction 104. One skilled in the art will appreciate that the junctions 104 described herein are not particularly limited to a specific direction of flow. Therefore, while the upstream and downstream portions are distinct from one another, the portions may be reversed so that the upstream side becomes the downstream side and vice versa simply by reversing the flow of fluid through the junction in use. Thus, in some embodiments, the junctions 104 are capable of being used in either flow direction.

The conduits 102 may preferably be flexible conduits suitable for use in medical environments. The conduits 102 may be constructed of a thermoset or a thermoplastic polymer. If a thermoset is used, silicones, polyurethanes, fluoroelastomers or perfluoropolyethers are preferred construction materials for the conduits. If a thermoplastic is used, C-Flex® tubing, block copolymers of styrene-ethylene-butylene-styrene, PureWeld, PVC, polyolefins, polyethylene, blends of EPDM and polypropylene (such as Santoprene™) are preferred construction materials. Semi-rigid thermoplastics including, but not limited to, fluoropolymers PFA, FEP, PTFR, THV, PVDF and other thermoplastics, such as polyamide, polyether sulfone, polyolefins, polystyrene, PEEK, also can be used in one or more portions or sections of the conduits to render them flexible. The multiple conduits 102 attached to the junction 104 may be made from different materials. In some embodiments, at least one of the conduits 102 attached to the junction may be a rigid conduit.

Figure 9:
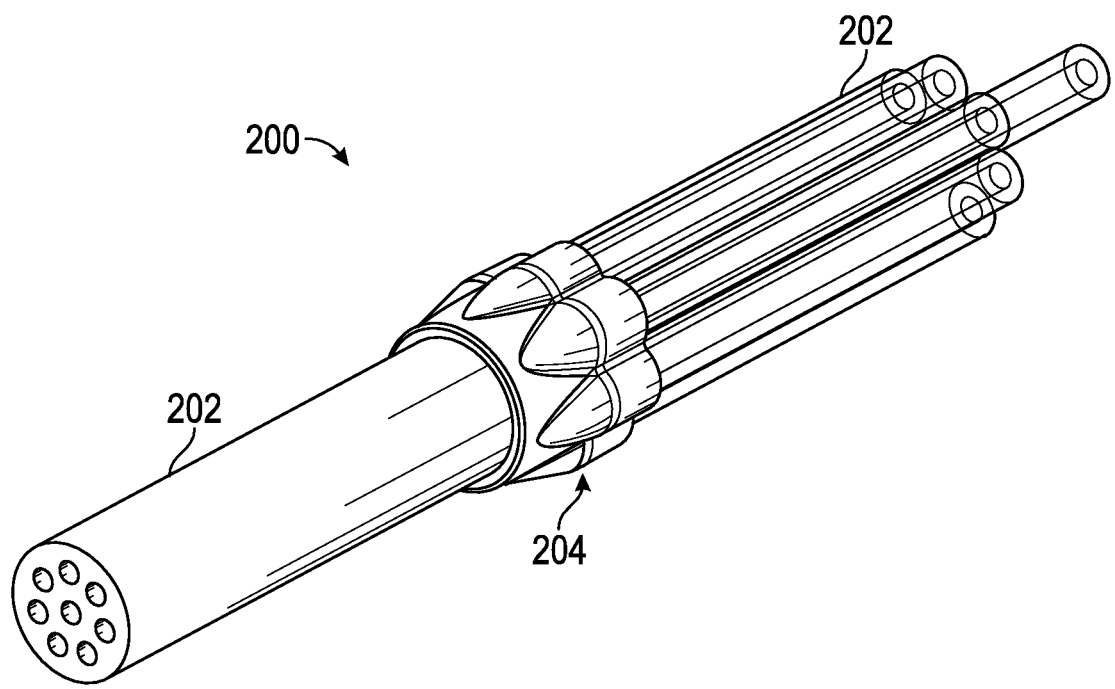

The conduits 102 may be various sizes in outer diameter and inner diameter depending upon the intended use of the fluid transfer assembly 100. The conduits 102 may be single-lumen conduits as shown in FIG. 1 or at least one of the conduits may be a multiple-lumen conduit as shown in FIG. 9. Where the conduit 102 includes multiple lumens, each lumen may be the same diameter or cross section, or the lumens may have more than one diameter or cross section within a single conduit 102.

Figure 1A:
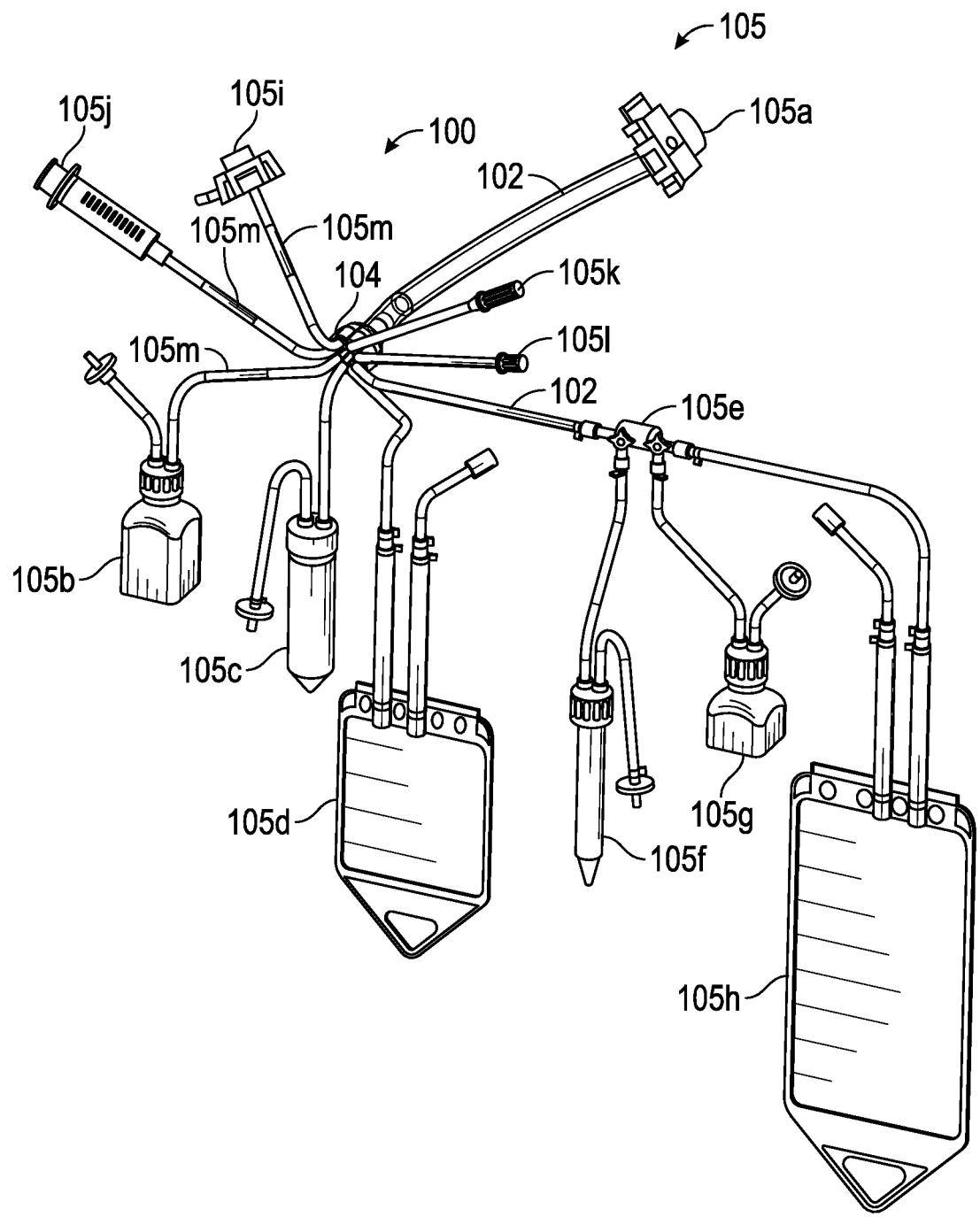
FIG. 1A illustrates the fluid transfer assembly of FIG. 1 with optional additional components.

As shown in FIG. 1A, the conduits 102 may lead from or to additional components 105, which may form part of the fluid transfer assembly. The additional components 105 may include one or more vessels including but not limited to containers, beakers, bottles, canisters, flasks, bags, receptacles, tanks, vats, vials, tubes, syringes, carboys, tanks, pipes and the like that are generally used to contain liquids, slurries, and other similar substances. The vessels may be closed by a MYCAP™, available from Sartorius Stedim North America. The conduits 102 may terminate in components 105 that include other aseptic connectors or fittings such as an AseptiQuik® connector available from Colder Products Company of St. Paul Minn., a BENCHMARK™ fitting available from Sartorius Stedim North America, an OPTA aseptic connector available from Sartorius Stedim North America, a ReadyMate connector available from GE Healthcare of Chicago Ill., or other terminus such as syringes, centrifuge tubes, or a plug. The illustrated embodiment of FIG. 1A includes a junction 104 and a plurality of conduits 102, which lead to the following optional and exemplary components: a ⅜" hose barb AseptiQuik® aseptic connector 105a; a 60 ml bottle assembly with MYCAP™ 105b; a 50 ml centrifuge tube assembly with MYCAP™ 105c; a 50 ml bag assembly 105d; a 2-gang stopcock valve assembly 105e with a 15 ml centrifuge tube 105f; a 30 ml bottle with MYCAP™ 105g, and a 500 ml purge bag 105h; an AseptiQuik® aseptic connector 105i; a 10 cc syringe 105j; a needleless access site with a cap 105k; and a capped luer fitting 105l. Some of the conduits 102 are provided with a Quickseal® 105m available from Sartorius Stedim North America. The example shown in FIG. 1A is for illustration of a small sample of the available vessels, connectors, and fittings available for use in fluid communication with the junction 104, and is not intended to limit the present disclosure.

Figure 2:
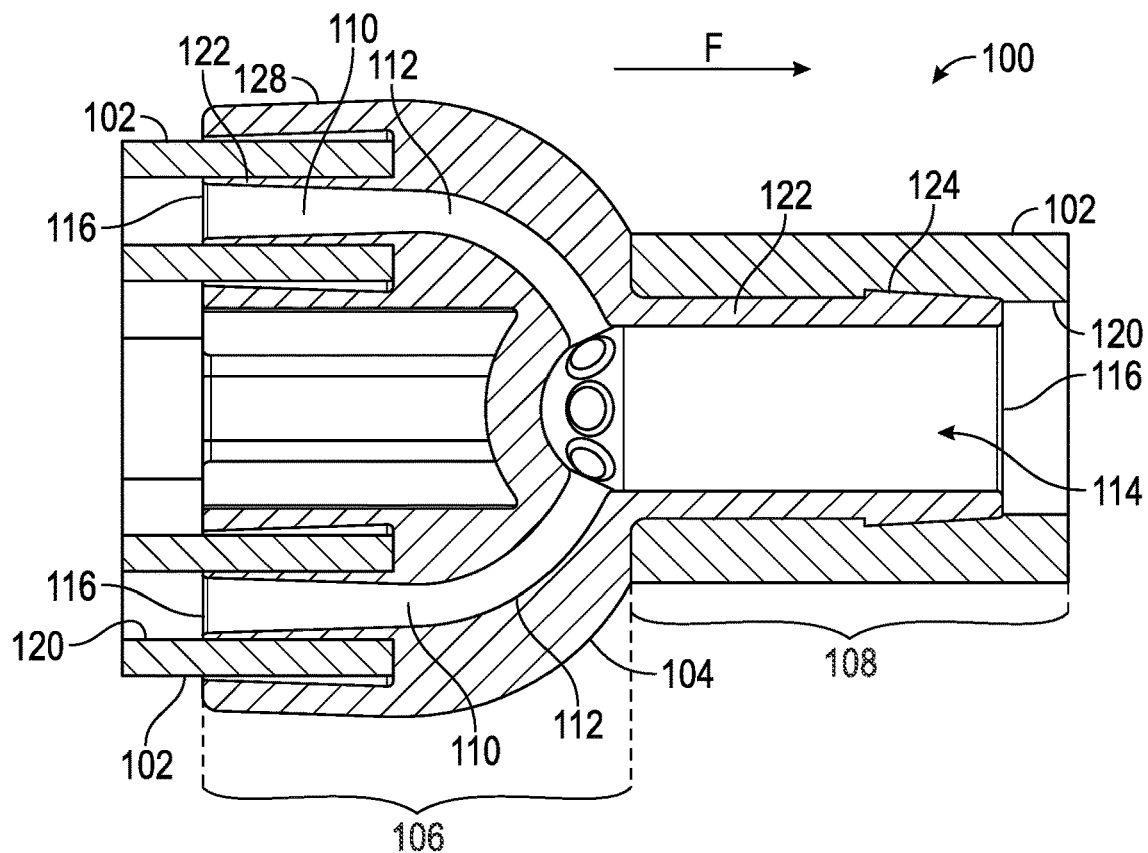
FIG. 2 illustrates a longitudinal cross section of the fluid transfer assembly of FIG. 1.
Figure 7:
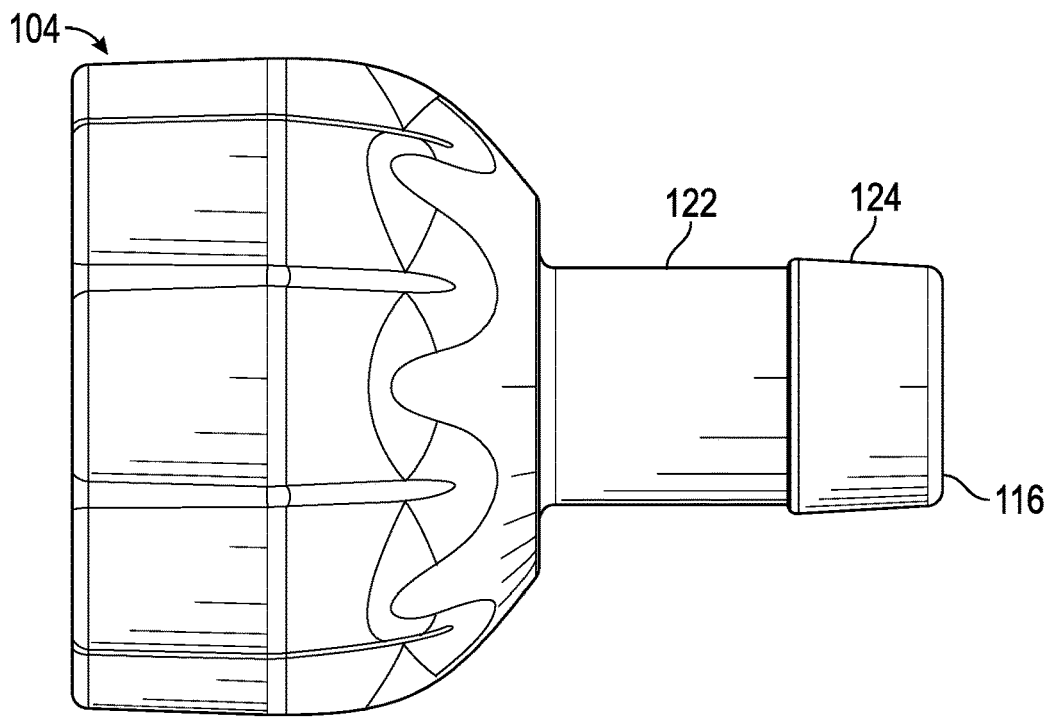
FIG. 7 illustrates a side view of the junction of the fluid transfer assembly of FIG. 1.

FIG. 2 shows a cross section of the junction 104. FIGS. 3-7 show various perspective and plan views of the junction 104 according to one embodiment. Notably, FIG. 7 shows a side view of the junction 104, which is shown as rotationally symmetric.

The junction 104 is preferably constructed as a unitary body of a one-piece construction. Once manufactured, the junction 104 is one-piece and does not require assembly of two or more components. One-piece unitary bodies are being formed from processes known in the art, such as injection molding, casting parts that are machined. As used herein, additive manufacturing processes also produce "unitary" bodies. In one embodiment, the junction 104 is made using an additive manufacturing process. As known in the art, additive manufacturing, also known as 3D printing, involves the creation of thin layers of substantially similar thickness being stacked upon one another to build material and form a body. Therefore, in some embodiments, the junction 104 of the present disclosure may be both a "unitary" construction and be formed from a plurality of layers of material, each layer being approximately the same thickness. In traditional additive manufacturing, the layers are built up, one on top of the layer below. Alternatively, in another embodiment, the present disclosure can employ CLIP technology, e.g., as offered by Carbon, Inc. of Redwood City, Calif., which, e.g., uses digital light synthesis to use patterns of light to partially cure a product layer by layer with the uncured material being cured to the bottom of the stack as a body of cured or semi-cured material is lifted from the reservoir of uncured material.

Suitable materials for the junction 104 include thermoplastics such as polyolefins, polypropylene, polyethylene, polysulfone, polyester, polycarbonate, and glass filled thermoplastics. The junction may also be made from thermosets such as epoxies, phenolics, silicone, copolymers of silicone and novolacs. Other suitable materials may include polyamide, PEEK, PVDF, polysulfone, cyanate ester, polyurethanes, and urethane methacrylate. Yet metallic materials, such as stainless steel, aluminum, titanium, etc., or ceramics, such as aluminum oxide, may be used. The present disclosure however is not limited to a junction made from any particular material(s) and any suitable materials or combinations thereof may be used without departing from the scope of the present disclosure.

Additive manufacturing techniques may allow for the creation of structures that may not be capable of being manufactured with traditional molding or machining steps. These structures can lead to a reduction in packaging space and a reduction in components, which can help to reduce leak points and reduce the costs of assembling the fluid transfer assembly 100.

In some embodiments, the junction 104 may be surface treated to affect appearance, hydrophobicity, and/or surface roughness. In bioprocesses particularly, minimizing surface roughness is preferred to minimize the potential for trapped bacteria. Examples of surface treatment can include metalizing with electroless nickel, copper, or other metal to fill in surface pits. A metalized surface may also improve adhesion and allow the junction 104 to be inductively heated. In another example, the junction 104 can be coated with an inorganic material, such as oxides of silicon (glass or glass like) or coated with organometallic materials. Silane coupling agents can be applied to the surface to change the surface hydrophobicity. If metallic, the junction 104 can be electropolished to improve surface roughness. The junction further can be polished using paste abrasives, such as paste abrasives available from Extrude Hone LLC of Pennsylvania.

With reference to FIG. 2, the junction 104 may be described as having an upstream portion 106 and a downstream portion 108. For this example, fluid is imagined as flowing from left to right across FIG. 2 as represented by the arrow F. As discussed above, the junction 104 is capable of using with the fluid flowing in the opposite direction. Therefore, the terms upstream and downstream are applied to the portions 106, 108 solely as one example, and may be reversed. The junction 104 provides a plurality of fluid pathways 110 between the upstream portion 106 and the downstream portion 108. Preferably, at least a portion of each pathway 110 is a curved segment 112. A curved segment is one that deviates from a straight line without sharp breaks or angularity. The curvature is preferred to be able to go from a small area (i.e. an end of a multi-lumen conduit, or a single-lumen conduit) to multiple independent conduits, which necessarily take up more space. To connect the two extremes in surface area, the shortest, smoothest path between them is believed to be a curved one. Traditionally, curved paths have not been used because curved paths are difficult or impossible to fabricate with conventional molding or machining processes.

The junction 104 of FIGS. 1-7 includes eight fluid pathways 110, though other suitable number of fluid pathways can be employed, such as four, five, six, seven, nine, ten, or more fluid pathways, without departing from the scope of the present disclosure. The fluid pathways 110 in the junction 104 share a common pathway segment 114. With fluid flowing in direction F, the fluid pathways 110 may be described as combining at the common pathway segment 114. If flow is reversed, fluid from the common pathway segment 114 may be described as splitting to create the eight illustrated fluid pathways 110.

In embodiments where the junction 104 is a unitary structure, the junction itself would be free from additional components. For example, the plurality of fluid pathways 110 from the upstream portion to the downstream portion may be free from diaphragms capable of restricting or stopping flow. In other words, valves would not be built into the junction to control the flow of fluid.

The junction 104 of FIGS. 1-7 includes eight apertures 116 on the upstream portion 106 corresponding to the eight fluid pathways 110 and one aperture 116 on the downstream portion 108 because all of the illustrated fluid pathways 110 combine into a single common pathway segment 114 that leads to the aperture 116 on the downstream portion of the junction. Therefore, in embodiments that involve a common pathway segment 114, the number of apertures 116 on the upstream portion 106 may not correspond with the number of apertures on the downstream portion 108. In some embodiments, not shown, the common pathway segment 114 may include an intermediate mixing chamber with an equal number of separate path segments extending upstream and downstream therefrom.

With reference to FIG. 2, a fluid conduit 102 is attached, and preferably sealed, to the junction 104 to place the one or more lumens 120 of the fluid conduit 102 in fluid communication with a respective fluid pathway 110. Preferably, the junction 104 includes corresponding male inserts 122 for each lumen 120 of each fluid conduit 102. The male inserts 122 are configured to be inserted into a respective lumen 120. According to the embodiment of FIG. 2, the male inserts 122 on the upstream portion 106 of the junction 104 include cylindrical tubular structures. In the illustrated embodiment, the plurality of male inserts 122 are substantially parallel with one another. As shown on the downstream portion 108, the male insert 122 may be provided with one or more barbs 124 or teeth. The junction 104 is shown in FIGS. 1-7 as attaching to each lumen 120 of each conduit 102 with a male insert 122. In some embodiments, the junction 104 may include female attachment portions that surround the exterior of one or more of the conduits 102. In other embodiments, a male insert 122 may be configured to abut an end of the conduit instead of being inserted therein. For example, the insert 122 may terminate with a flange suitable for use with tri-clamps as well-known in the art of bioprocessing equipment. If a tri-clamp is used, the clamp union may be governed by ASME-BPE 2016.

Figure 3:
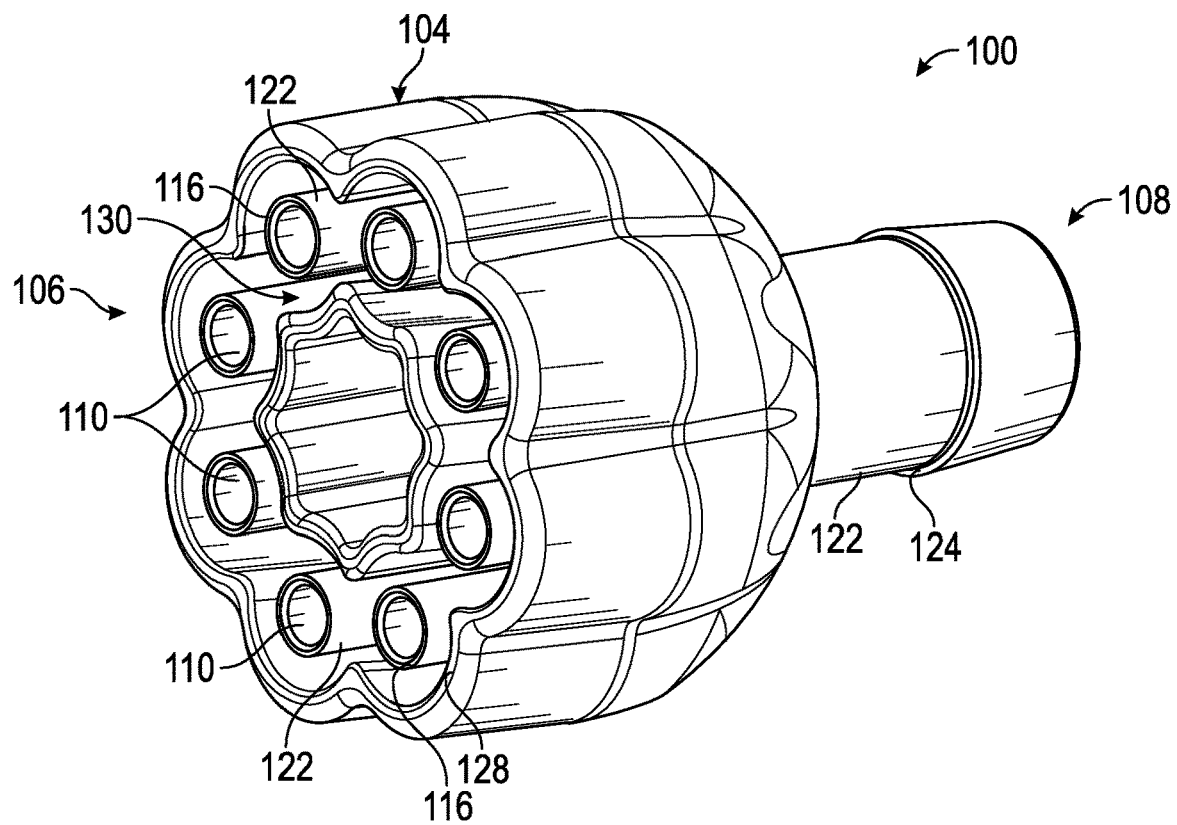
FIG. 3 illustrates a first perspective view of the junction of the fluid transfer assembly of FIG. 1.
Figure 4:
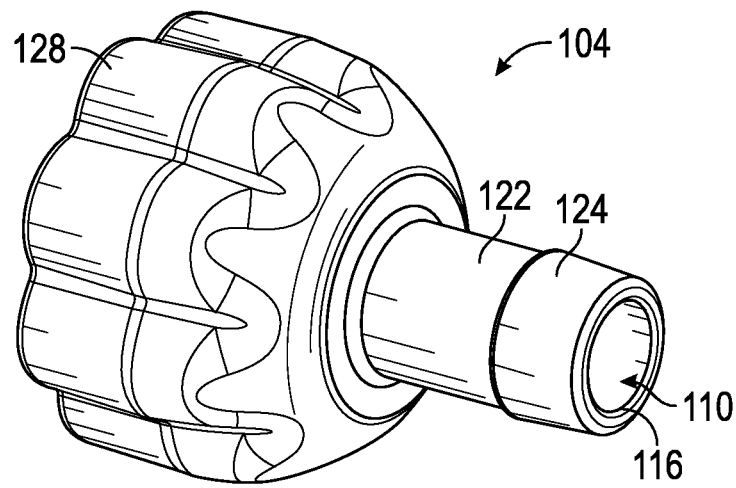
FIG. 4 illustrates a second perspective view of the junction of the fluid transfer assembly of FIG. 1.
Figure 5:
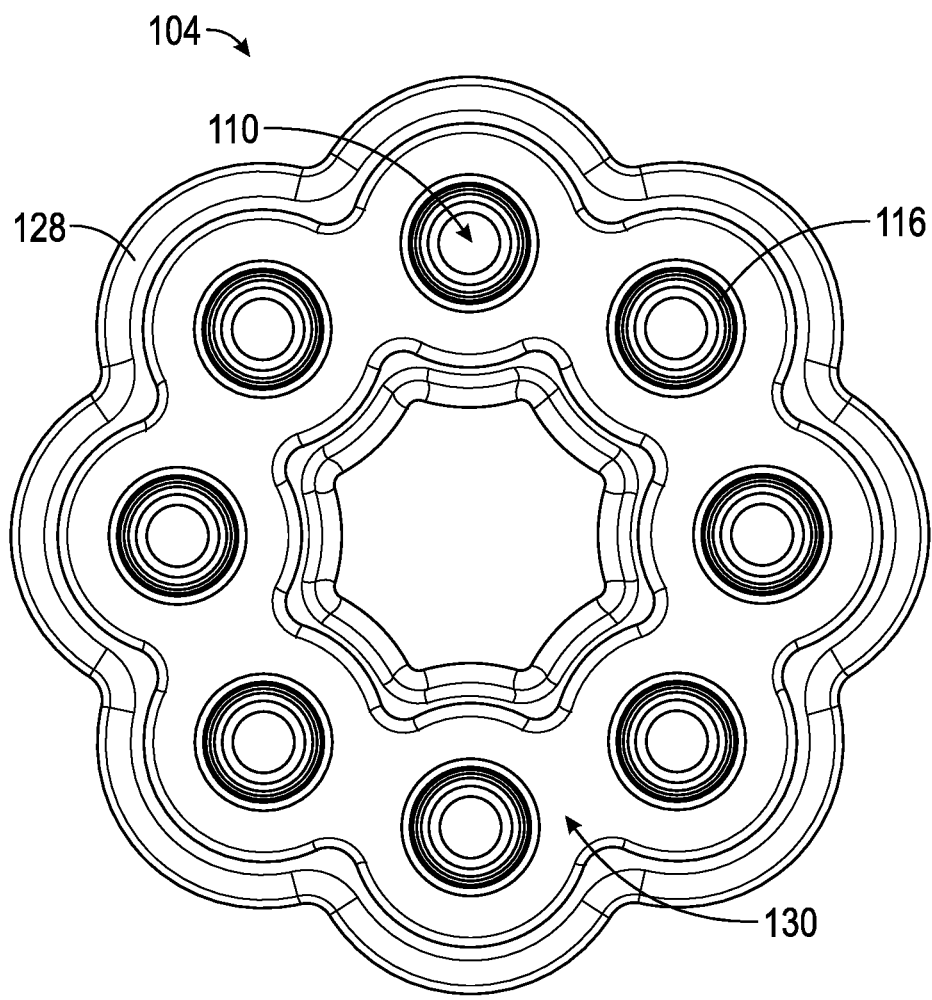
FIG. 5 illustrates a first end view of the junction of the fluid transfer assembly of FIG. 1.
Figure 6:
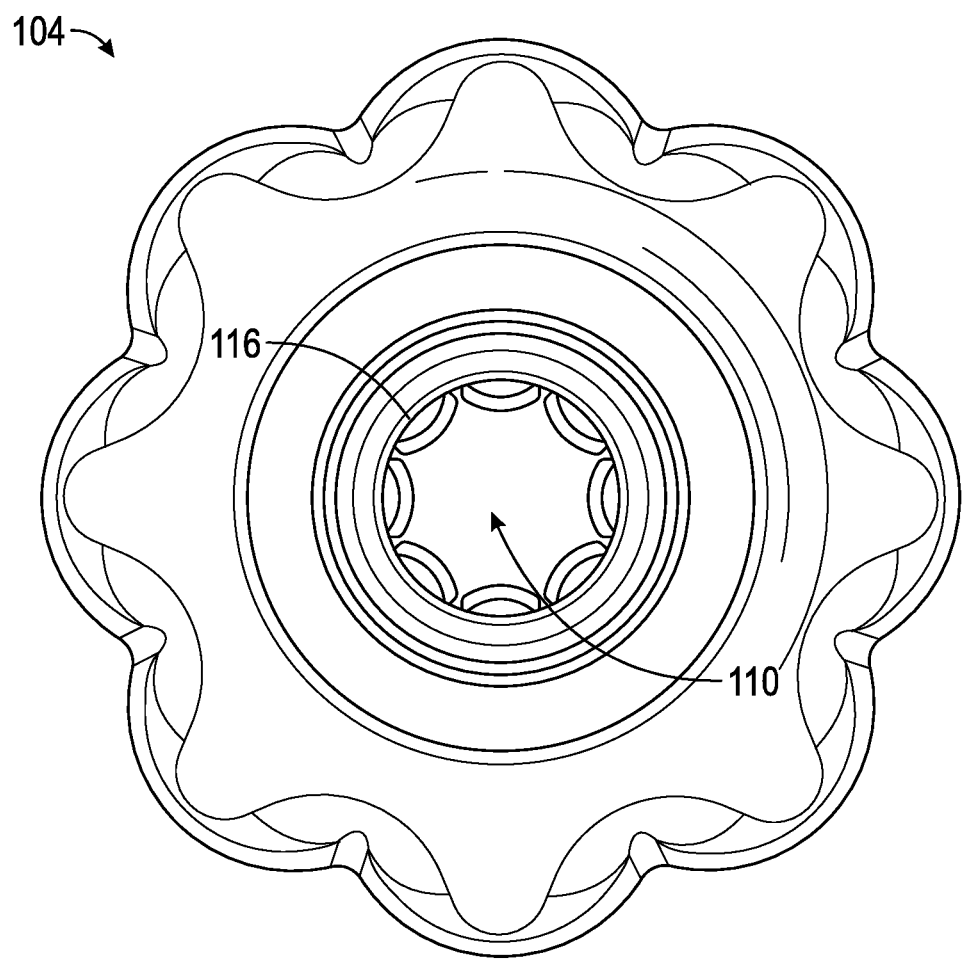
FIG. 6 illustrates a second end view of the junction of the fluid transfer assembly of FIG. 1.

Turning to FIGS. 2 and 3, the plurality of male inserts 122 on the upstream portion of the junction 104 are surrounded by a peripheral wall 128, which also may be referred to as a flange or skirt. The peripheral wall 128 creates a cavity 130 comprised of the interstitial space between the male inserts 122. In one embodiment, the peripheral wall 128 is scalloped to closely follow the outline of a plurality of fluid conduits 102 attached to the corresponding portion of the junction 104.

In some embodiments, the peripheral wall 128 is configured to contain an adhesive or a curable material used to secure the fluid conduits 102 to the junction 104. In one embodiment, silicone adhesive (LIM 8040) may be placed within the peripheral wall 128 of the junction 104 and then a multi-lumen silicone conduit 102 may be placed into the cavity. In one variation, the adhesive can be heat cured at about 150° C. for about 30 minutes, though other temperatures (e.g., about 140° C. to about 160° C. or other numbers therebetween) and durations (e.g., about 20 to about 40 minutes or other suitable times therebetween) may be used without departing from the scope of the present disclosure. In some embodiments, the curable material may provide a cast seal. If used, the cast seal surrounds and secures the conduits 102 to the junction 104. In an embodiment, the cast seal is constructed from a self-leveling, pourable silicone such as room-temperature-vulcanizing ("RTV") silicone. The RTV silicone may be a two-component system (base plus curative) ranging in hardness from relatively soft to a medium hardness, such as from approximately 9 Shore A to approximately 56 Shore A. Suitable RTV silicones include Wacker® Elastocil® RT 622, a pourable, addition-cured two-component silicone rubber that vulcanizes at room temperature (available from Wacker Chemie AG), and Rhodorsil® RTV 1556, a two-component, high strength, addition-cured, room temperature or heat vulcanized silicone rubber compound (available from Blue Star Silicones). Both the Wacker® Elastocil® RT 622 and the Bluestar Silicones Rhodorsil® RTV 1556 have a viscosity of approximately 12,000 cP (mPa·s). The aforementioned silicones and their equivalents offer low viscosity, high tear cut resistance, high temperature and chemical resistance, excellent flexibility, low shrinkage, and the ability to cure a cast silicone seal at temperatures as low as approximately 24° C. (approximately 75° F.). The cast seal may also be constructed from dimethyl silicone or low temperature diphenyl silicone or methyl phenyl silicone. An example of phenyl silicone is Nusil MED 6010. Phenyl silicones are particularly appropriate for cryogenic applications. In another embodiment, the casting agent is a perfluoropolyether liquid. A preferred perfluoropolyether liquid is Sifel 2167, available from Shin-Etsu Chemical Co., Ltd. of Tokyo, Japan. In some instances, a primer may be used to promote bonding of the cast seal to the conduits 102 and the junction 104. Suitable primers are SS-4155 available from Momentive™, Med-162 available from NuSil Technology, and Rodorsil® V-O6C available from Bluestar Silicones of Lyon, France.

The conduits 102 may be fixed to the junction 104, such as being secured around a male insert 122 using one or more of several other known attachment techniques. For example, the conduit 102 shown attached to the male insert 122 on the downstream portion 108 of the junction 104 of FIGS. 1 and 2 may be retained by friction and supplemented by the barb shown on the male insert. Additionally, or alternatively, several clamping methods are known in the art, including Oetiker clamps, hose clamps, cable ties, etc. The conduits 102 could also be welded to the junction 104. In some embodiments, the junction 104 may be fashioned with receivers for conduits 102 which facilitate a quick connect attachment similar to the MPC series of fittings by Colder Products Company of St. Paul, Minn.

Figure 8:
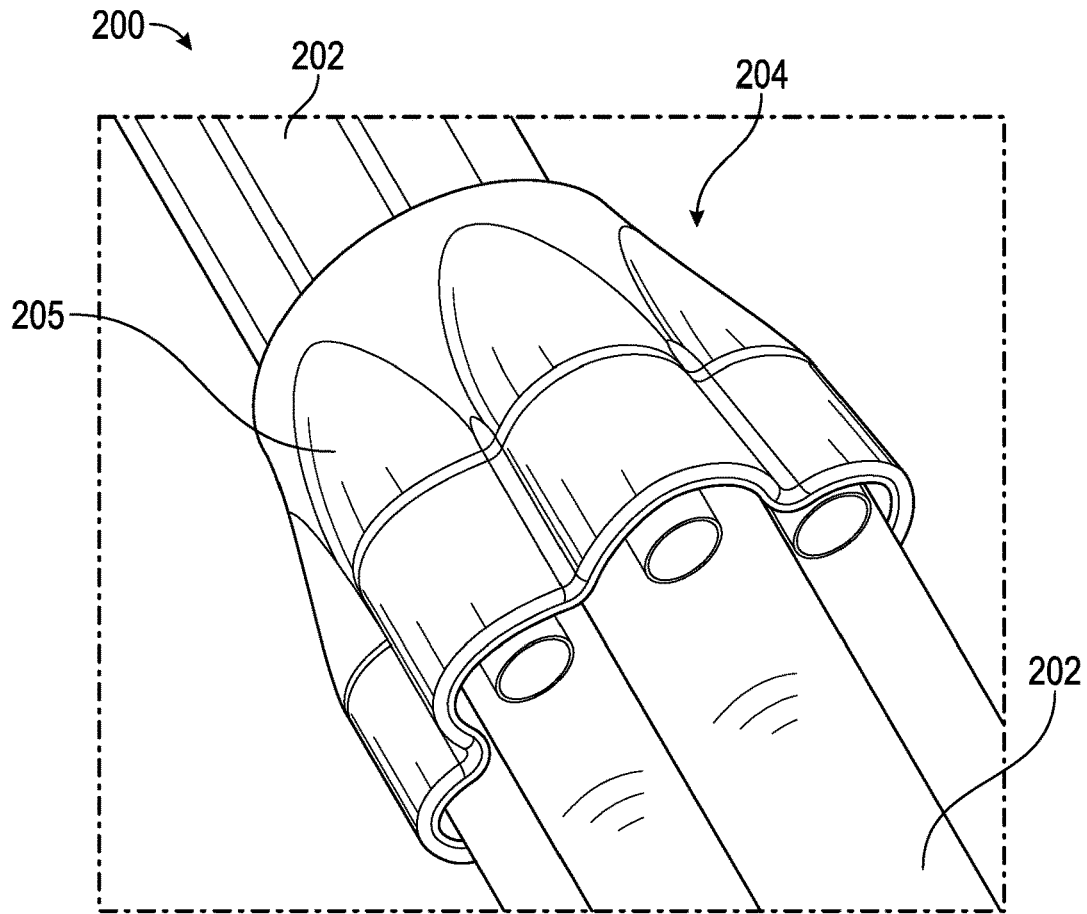
FIGS. 8 and 9 illustrate perspective views of a fluid transfer assembly according to a second embodiment.

FIGS. 8-15 illustrate a fluid transfer assembly 200 with fluid conduits 202 and a junction 204. As shown in FIGS. 8-9, one of the fluid conduits 202 is a multi-lumen conduit. The illustrated multi-lumen conduit has a central lumen configured to be sealingly joined to the junction 204 and in fluid communication with a fluid pathway 210. The junction 204 is substantially similar to the junction 104 illustrated in FIGS. 1-7 but is configured with a central fluid pathway 210 and seven peripheral fluid pathways to correspond with the arrangement of lumen 220 through the multi-lumen conduit. The central fluid pathway 210 does not have a curved segment 212 but the peripherally arranged fluid pathways do. Instead of a barb fitting as shown in FIG. 2, the junction 204 includes peripheral walls 228 on each of the upstream and downstream portions 206, 208 of the junction surrounding a plurality of male inserts 222.

Figure 16:
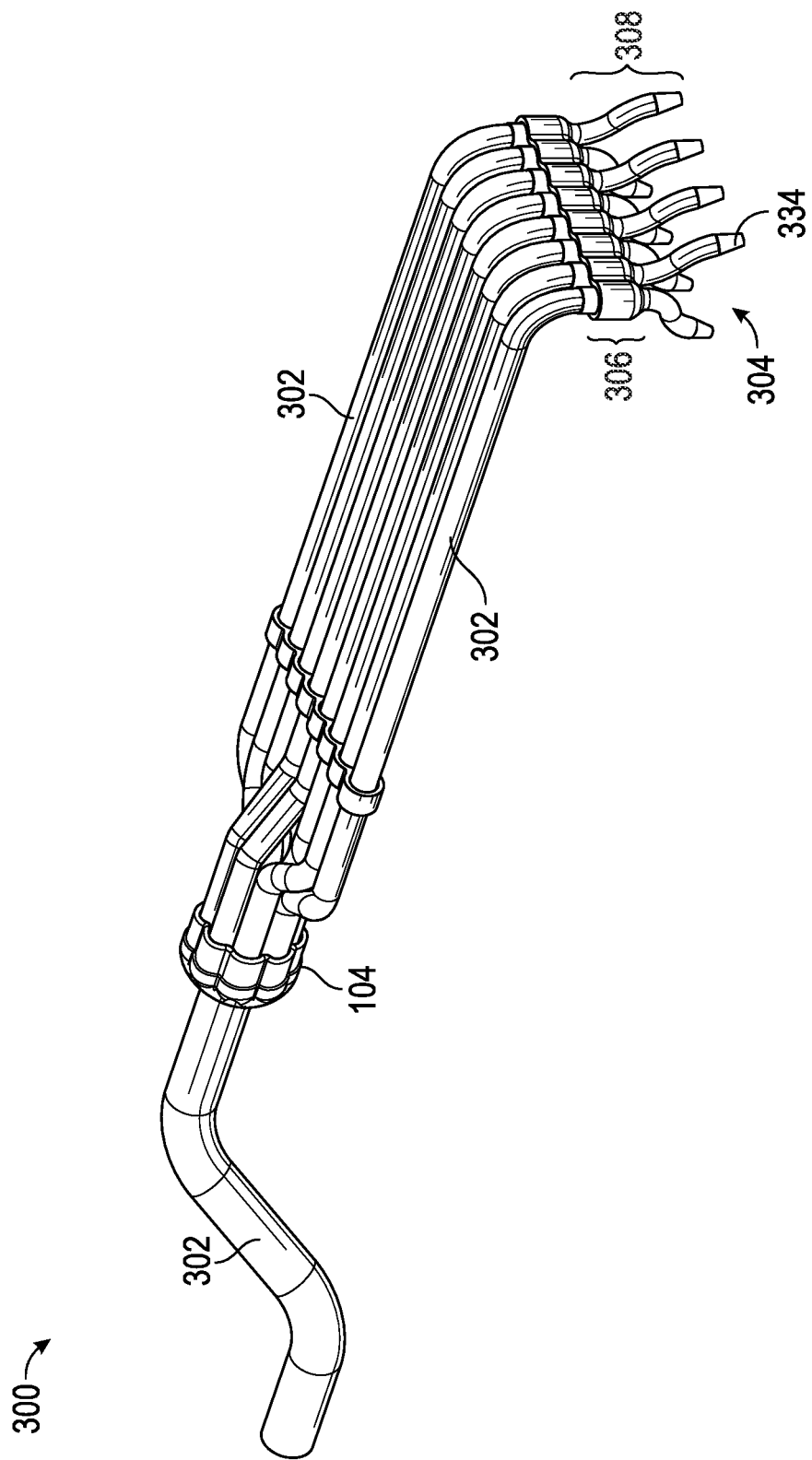
FIG. 16 illustrates a fluid transfer assembly according to a third embodiment.
Figure 17:
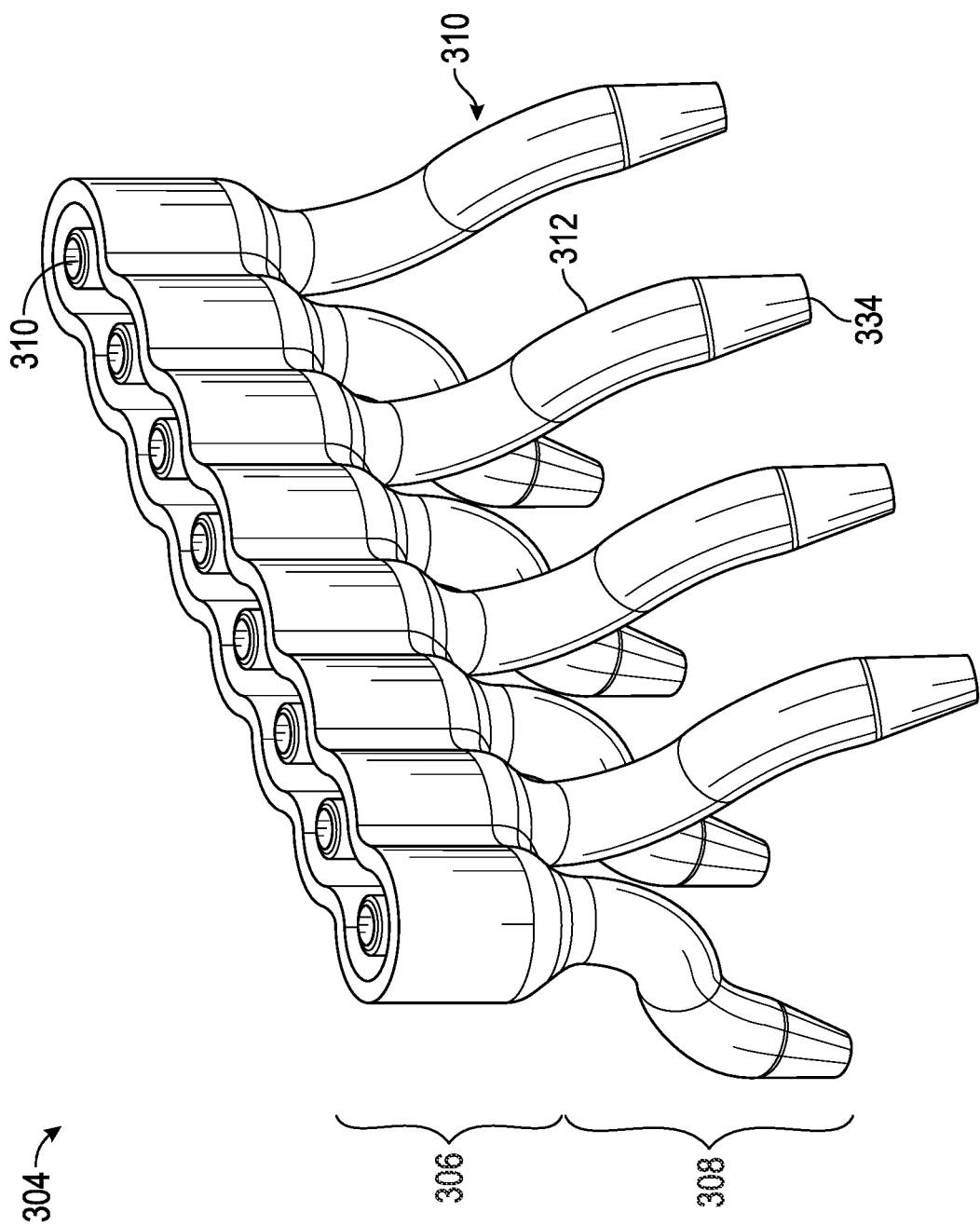
FIGS. 17, 18, 19, 20, and 21 illustrate multiple views of a junction used in the fluid transfer assembly of FIG. 16.
Figure 18:
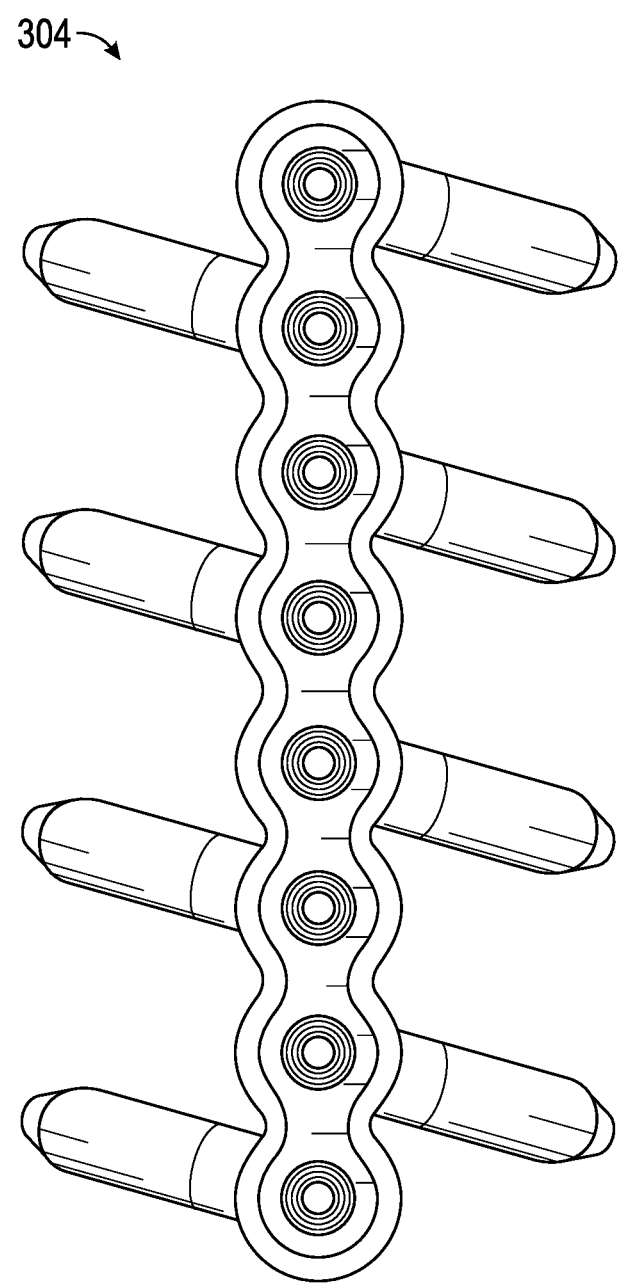
Figure 19:
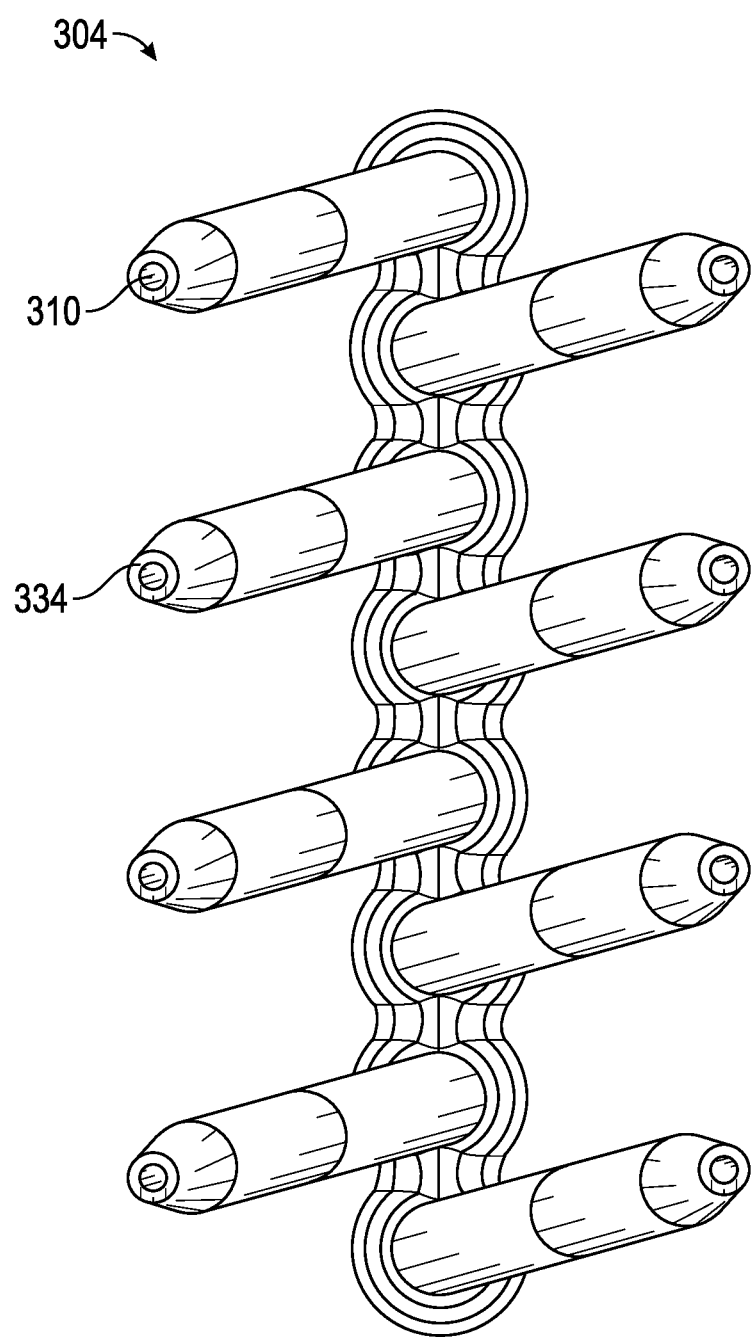
Figure 20:
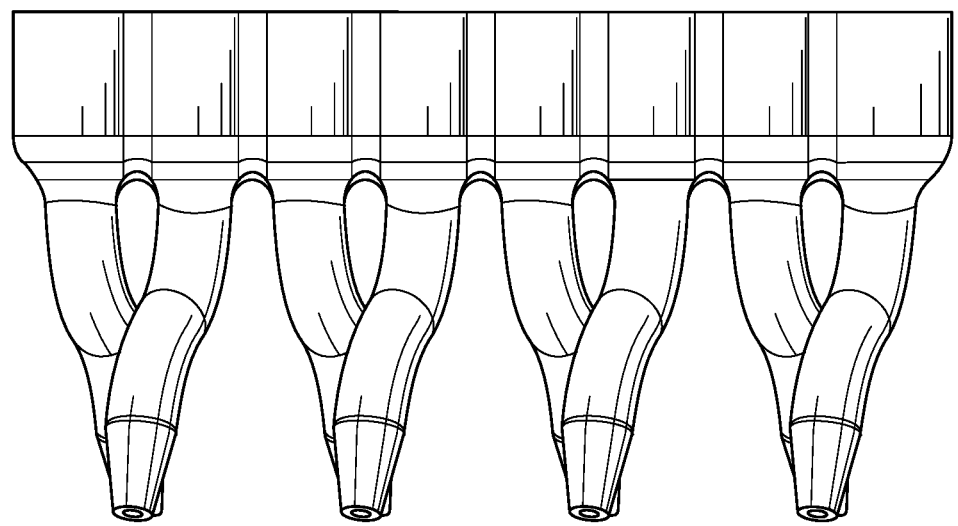
Figure 21:
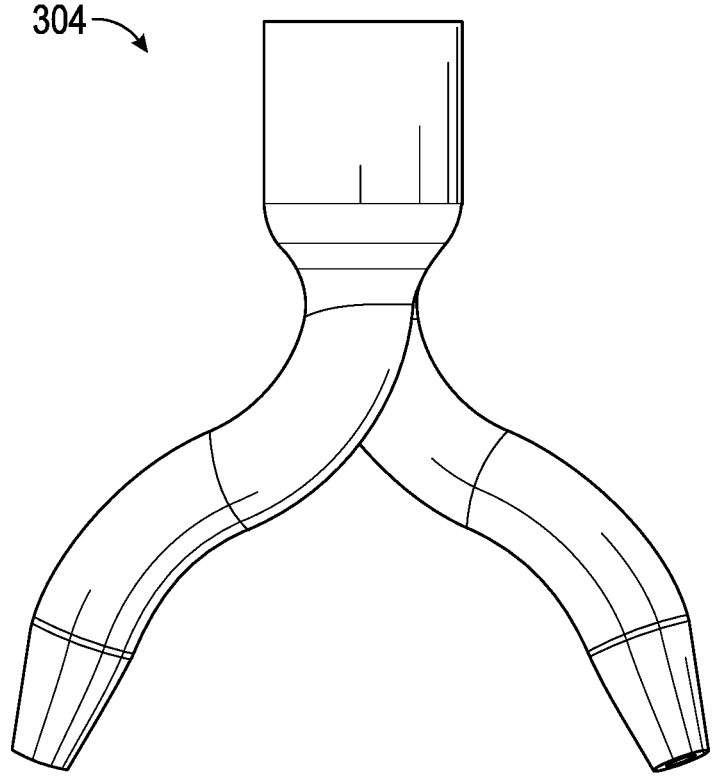

FIG. 16 shows a third fluid transfer assembly 300. The fluid transfer assembly 300 includes a junction 304 sealingly attached to the ends of a plurality of conduits 302, which themselves are coupled to a junction 104 or a junction 204 as discussed above. FIGS. 17-21 include a perspective view, top view, bottom view, major side view and minor side view respectively of the junction 304. Unlike the junctions 104, 204 of the first and second embodiment, the third embodiment of the junction 304 has a plurality of fluid pathways 310, each with a curved segment 312, but each pathway ends in a nozzle 334, thereby creating a predetermined upstream portion 306 and downstream portion 308 for the junction 304.

Figure 22:
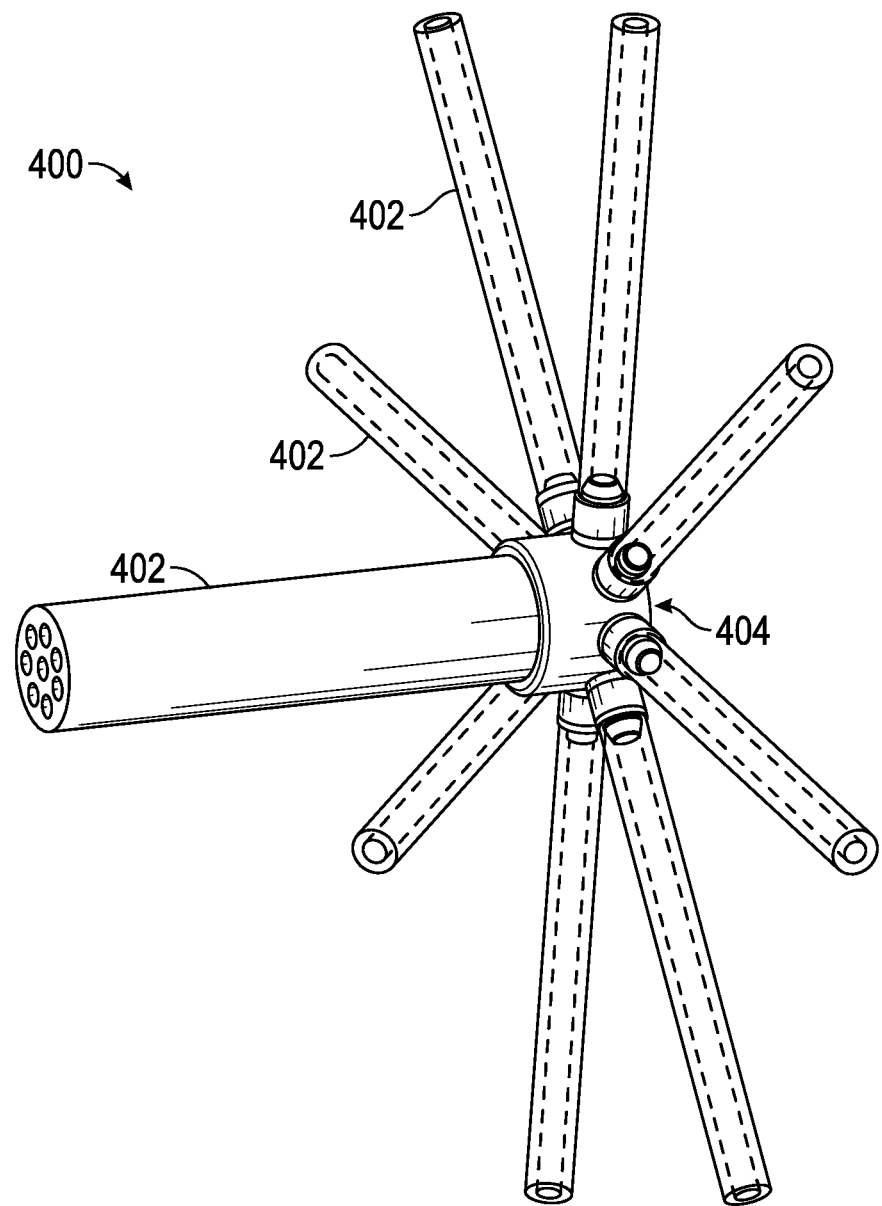
FIG. 22 illustrates a fluid transfer assembly according to a fourth embodiment.

FIG. 22 shows a fourth fluid transfer assembly 400. The fluid transfer assembly 400 includes a plurality of fluid conduits 402, including a multi-lumen conduit on one end of a junction 404 and a plurality of single-lumen conduits arranged radially around a central axis of the junction. FIGS. 23-29 show a variety of views of the junction 404. The junction 404 includes a plurality of male inserts 422 on the upstream portion 406 and a plurality of male inserts 422 on the downstream portion 408. The male inserts 422 on the downstream portion are arranged radially and illustrated in the form of barb fittings.

The junction 404 includes an optional indicia 440 adjacent to a single one of the plurality of male inserts 422, the indicia is adjacent to the single one of the male inserts that corresponds with a fluid pathway 410 accessible along the central axis of the junction 404. The indicia 440 is illustrated as a boss with an oval shape, but the indicia may be any marking capable of providing notice to a user of the male insert 422 that corresponds with a central one of the male inserts 122 on the upstream portion 406. Because the pathways 410 corresponding with the peripherally arranged inserts 422 of the upstream portion 406 may be apparent to the user, only a single indicia 440 with a single insert 422 may be necessary. In other embodiments, however, each pathway 410 may be labeled.

Figure 10:
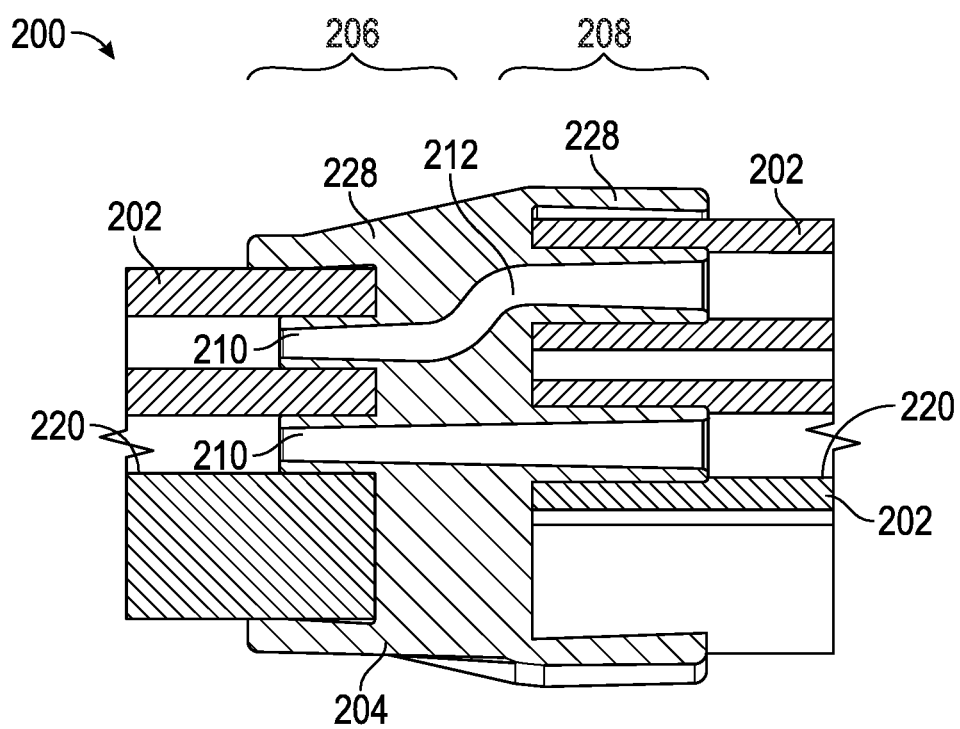
FIG. 10 illustrates a longitudinal cross section of the fluid transfer assembly of FIGS. 8 and 9.
Figure 11:
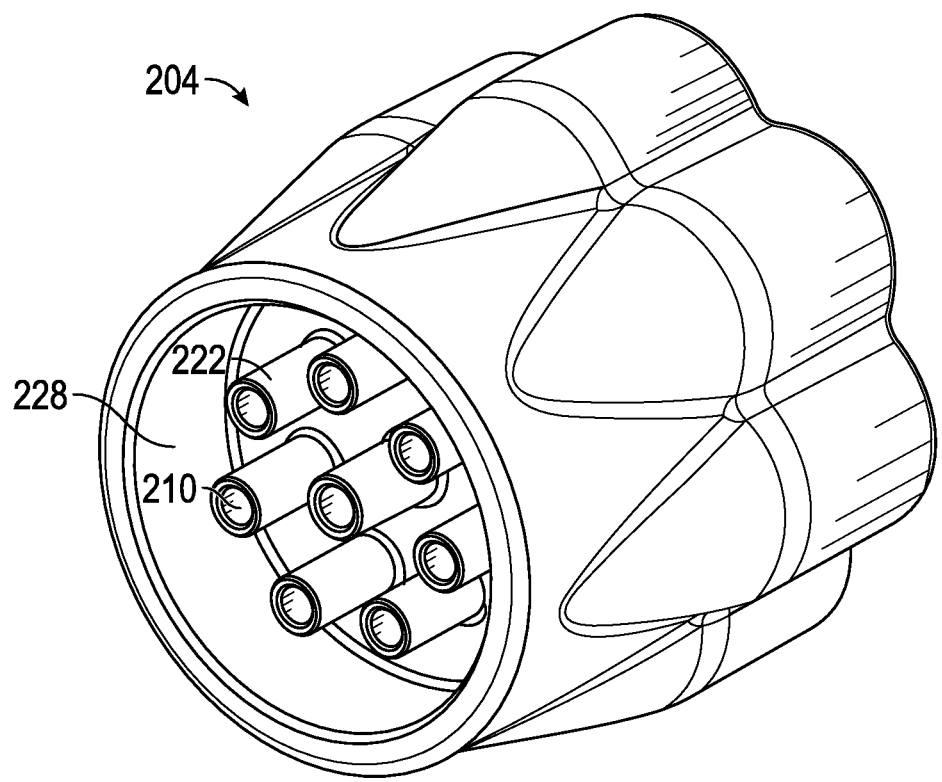
FIGS. 11 and 12 illustrate perspective views of a junction according to the embodiment of FIGS. 8 and 9.
Figure 12:
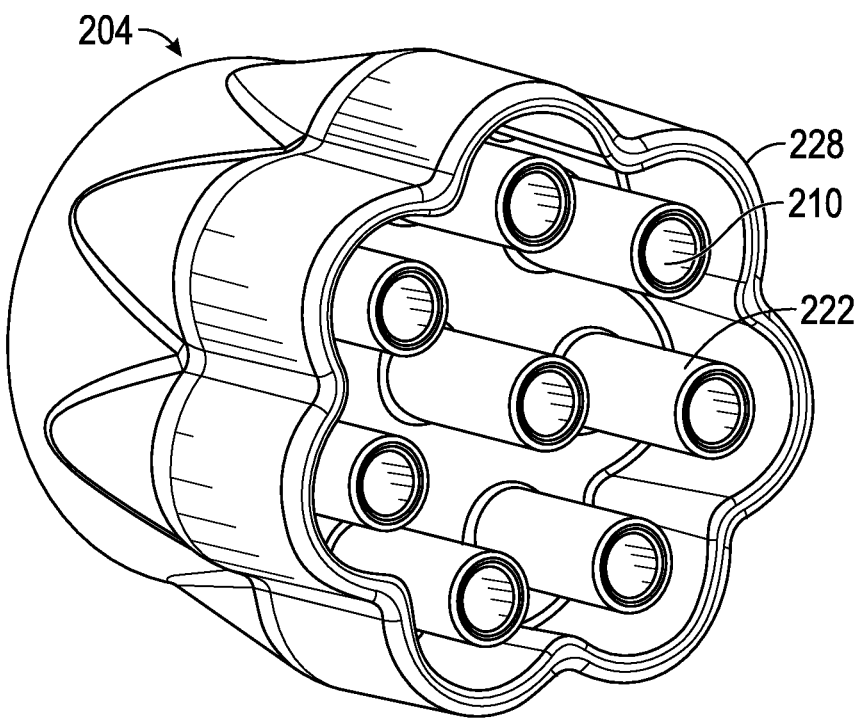
Figure 13:
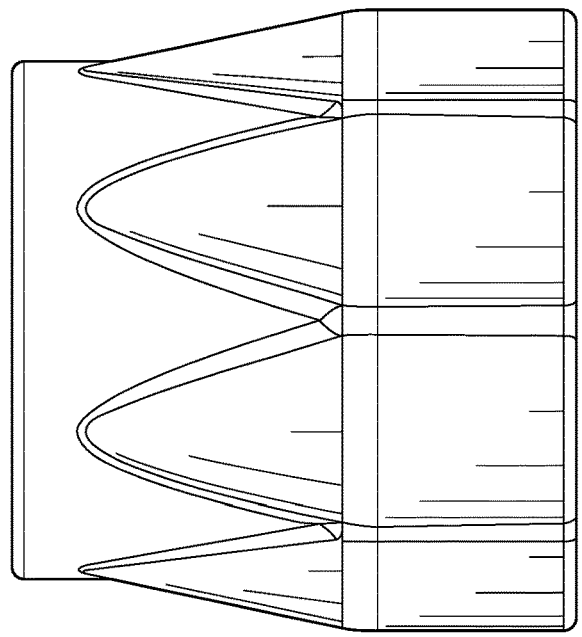
FIGS. 13, 14, and 15 illustrate a side view and two end views respectively of the junction of FIGS. 11 and 12.
Figure 14:
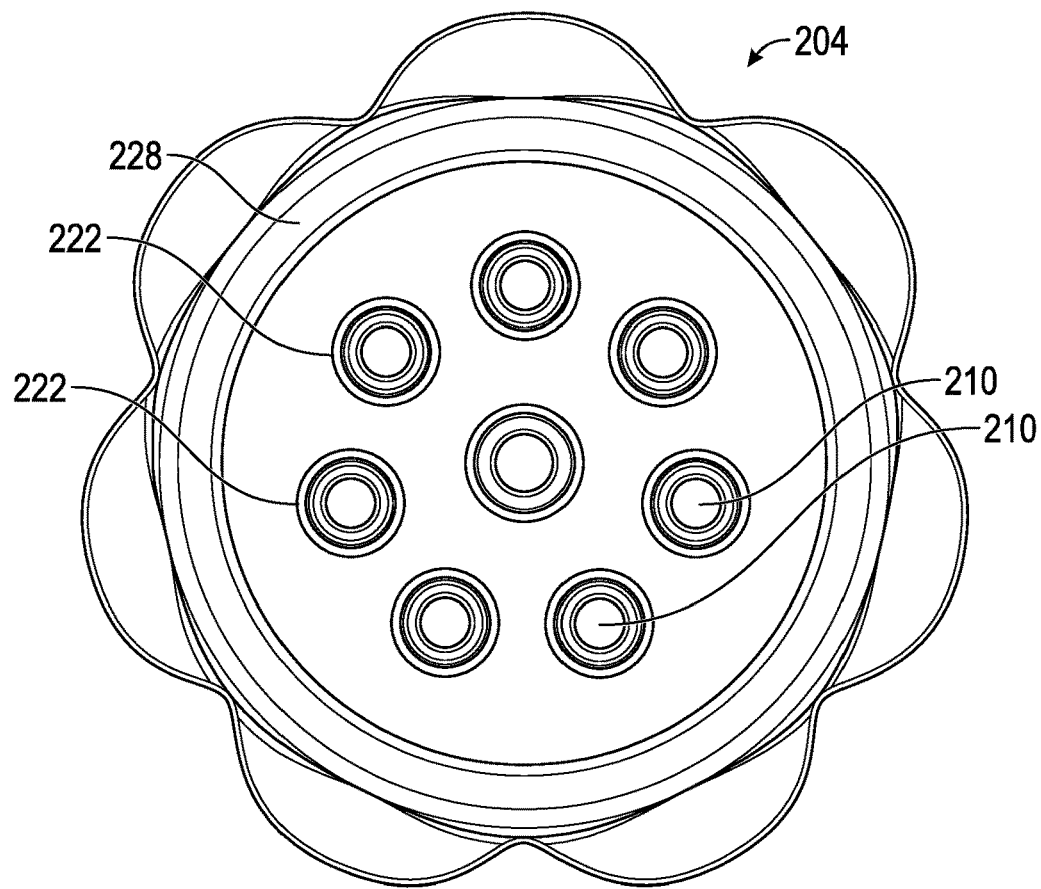
Figure 15:
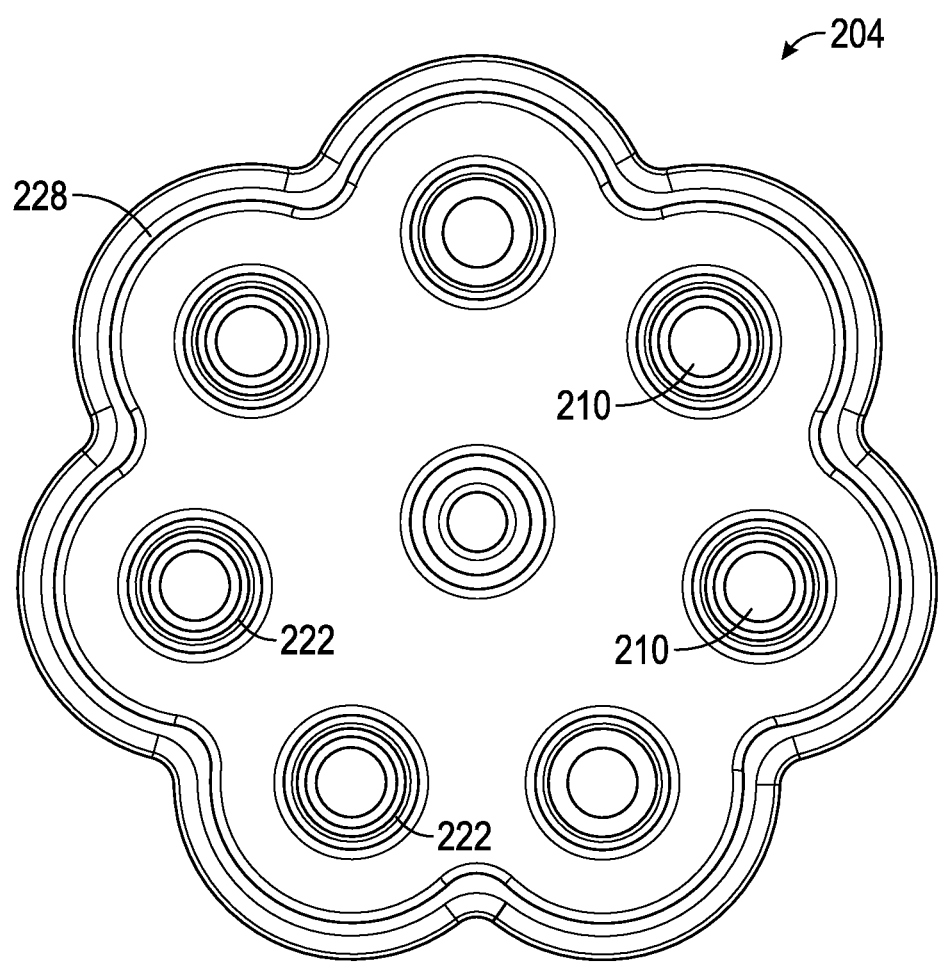
Figure 23:
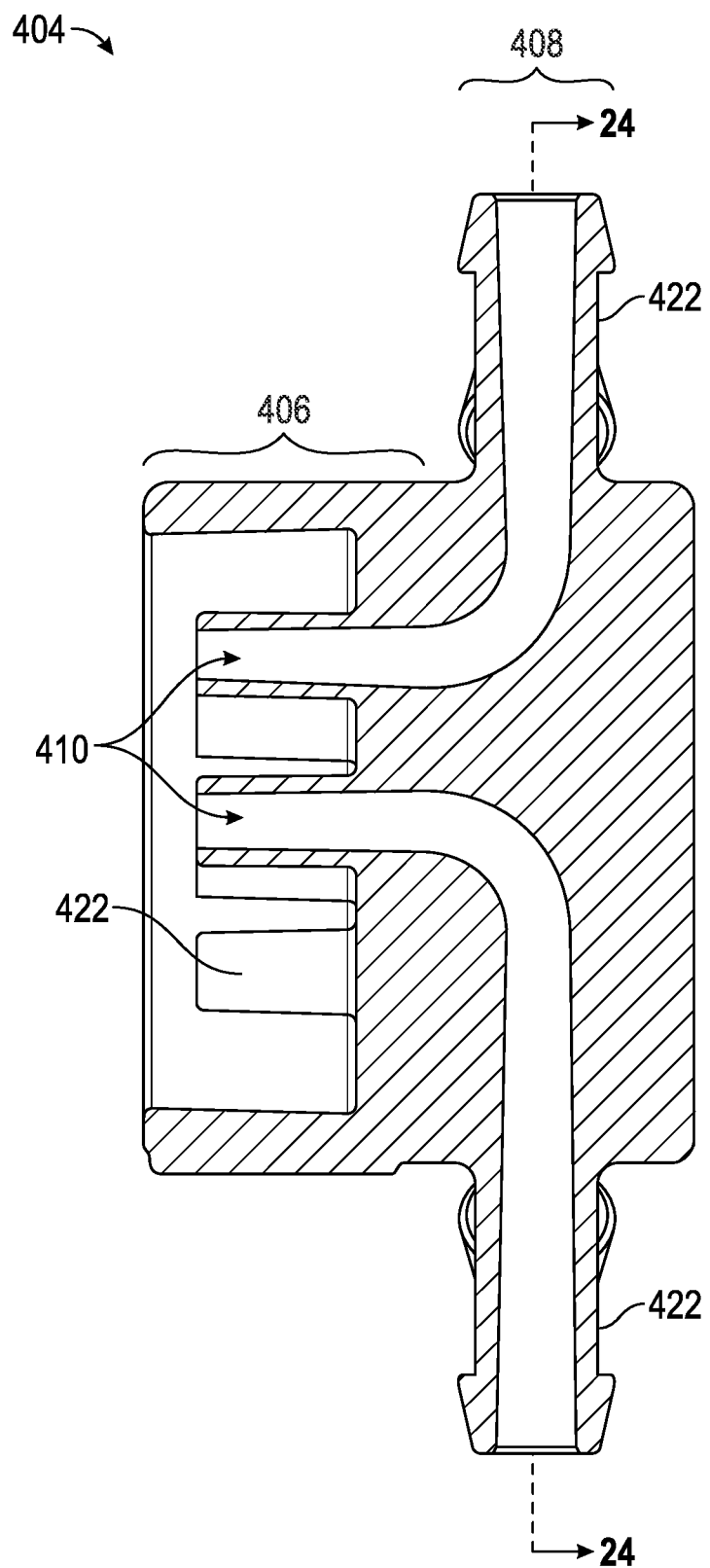
FIGS. 23, 24, 25, 26, 27, 28, and 29 illustrate several views of the junction of the fluid transfer assembly of FIG. 22.
Figure 24:
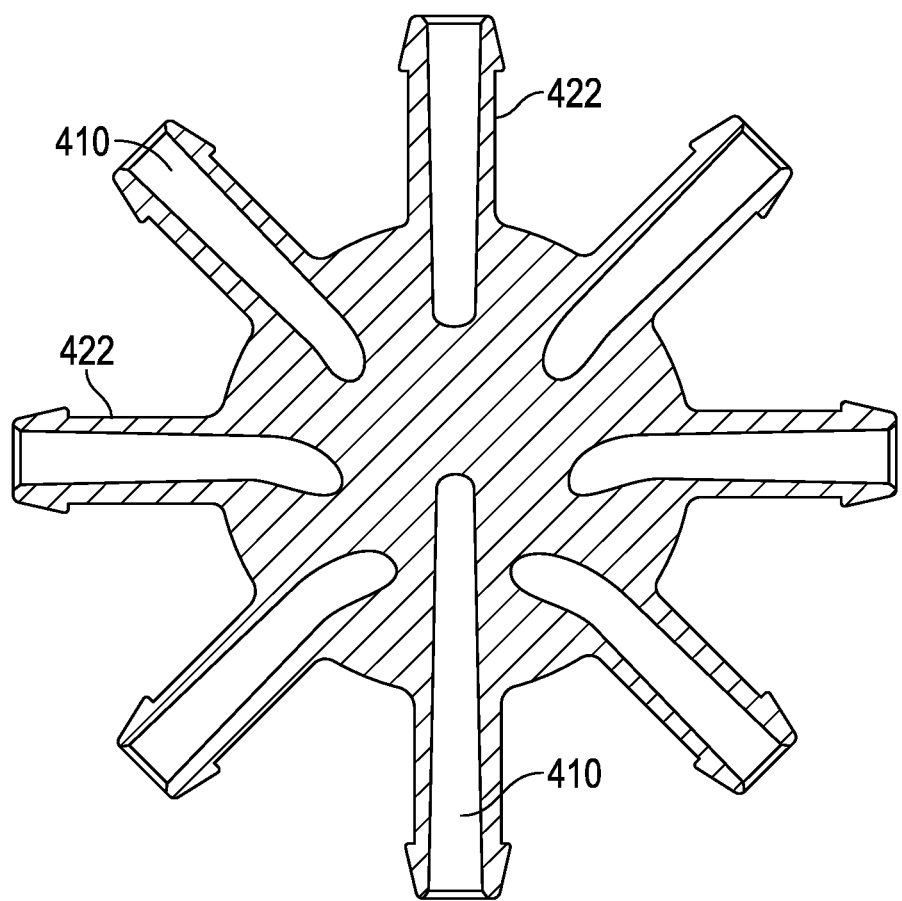
Figure 25:
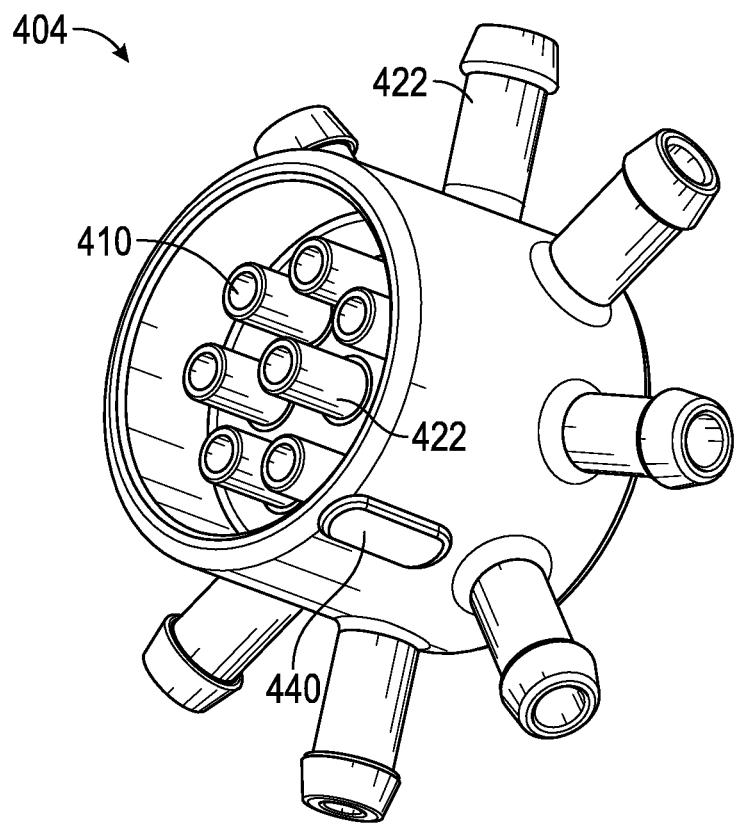
Figure 26:
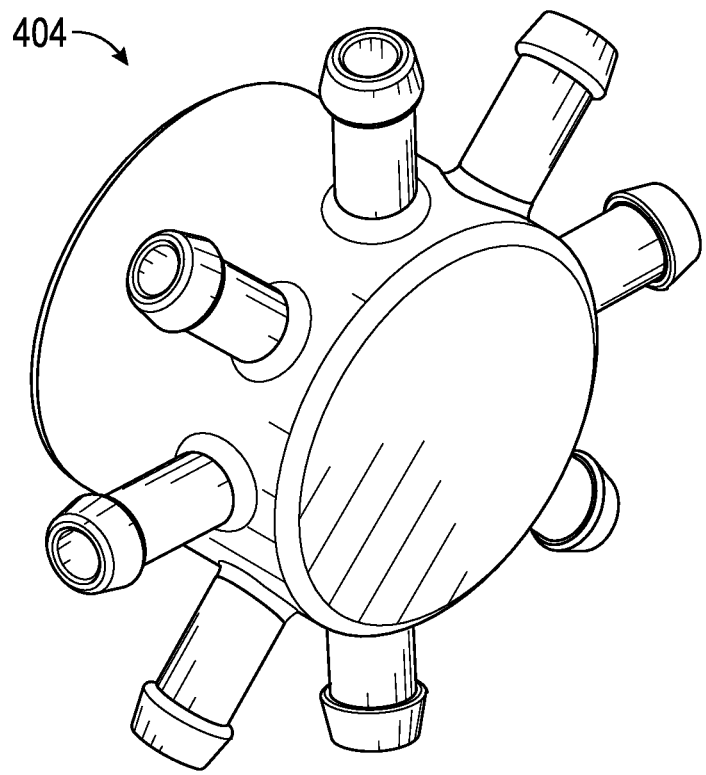
Figure 27:
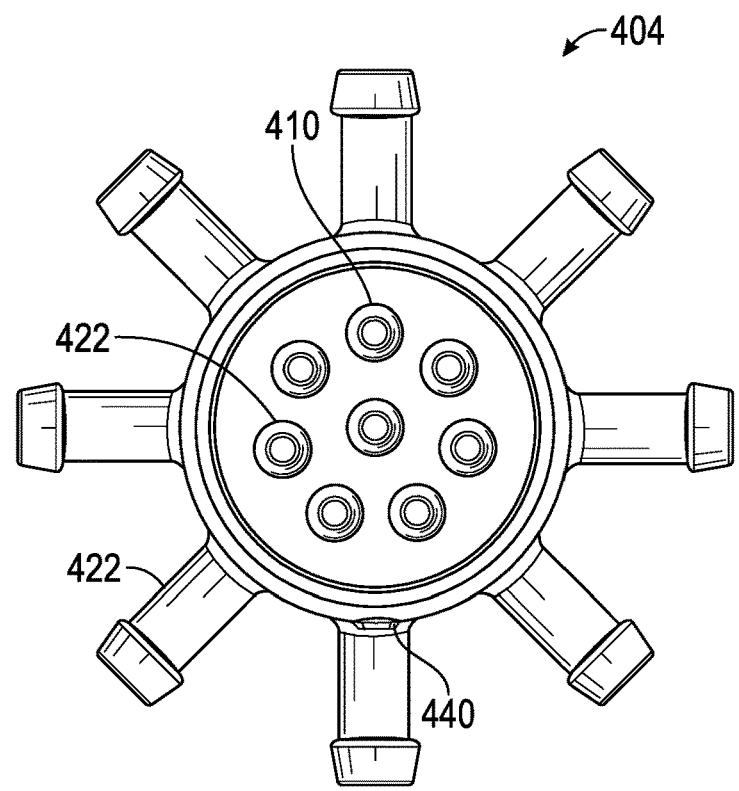
Figure 28:
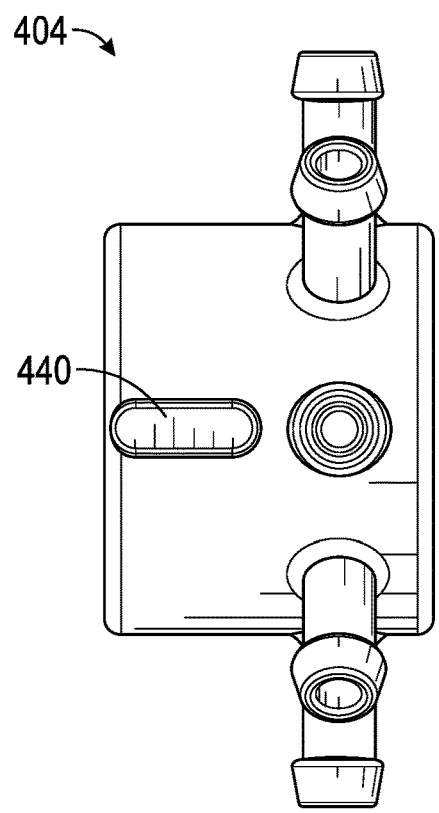
Figure 29:
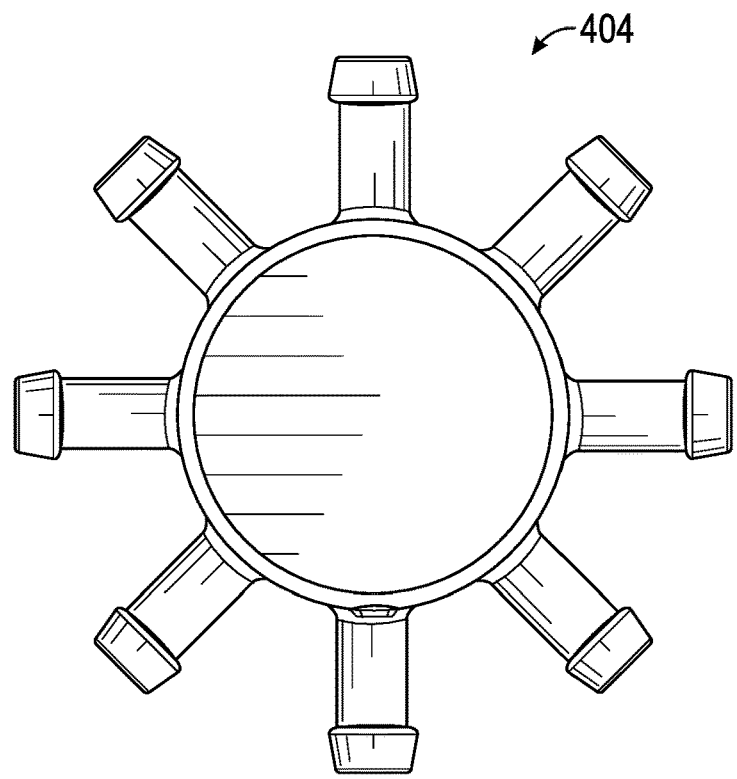
Figure 30:
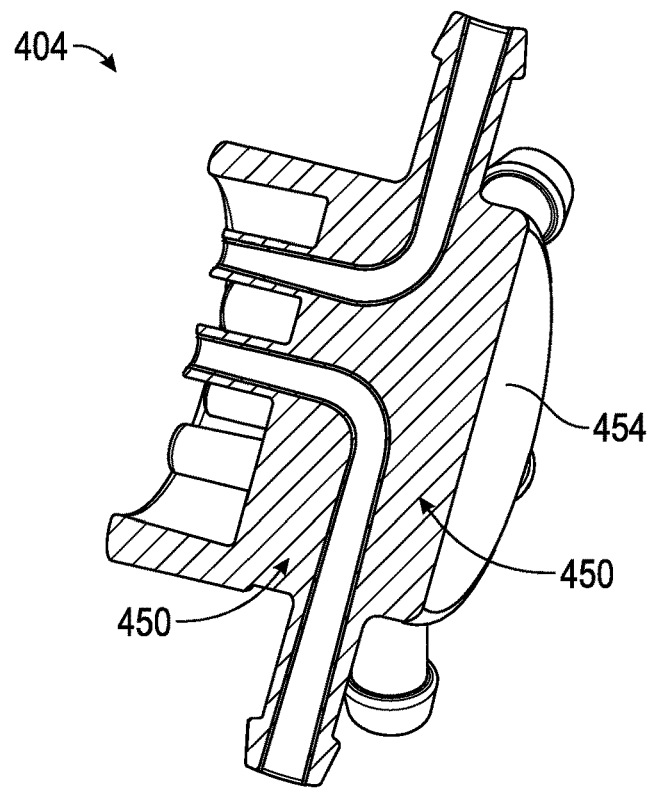
FIG. 30 illustrates an alternative cross section of the junction according FIGS. 23-29.
Figure 31:
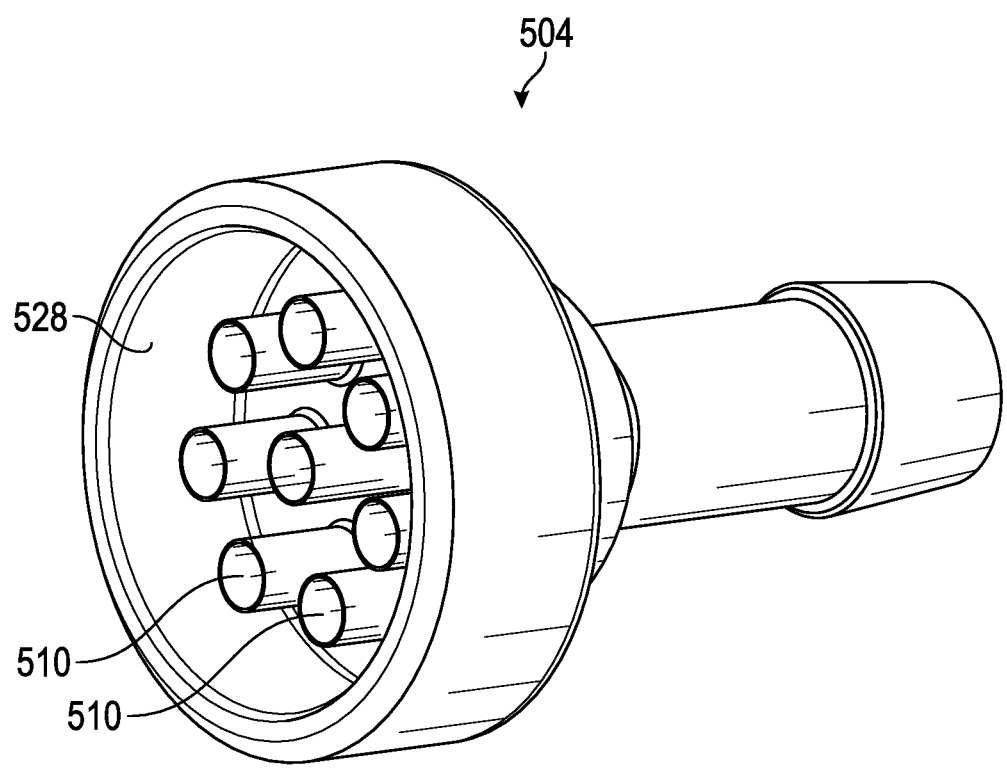
FIGS. 31, 32, 33, 34, 35, and 36 show multiple views of a junction suitable for use with the fluid transfer assemblies of FIGS. 1 and 8.
Figure 32:
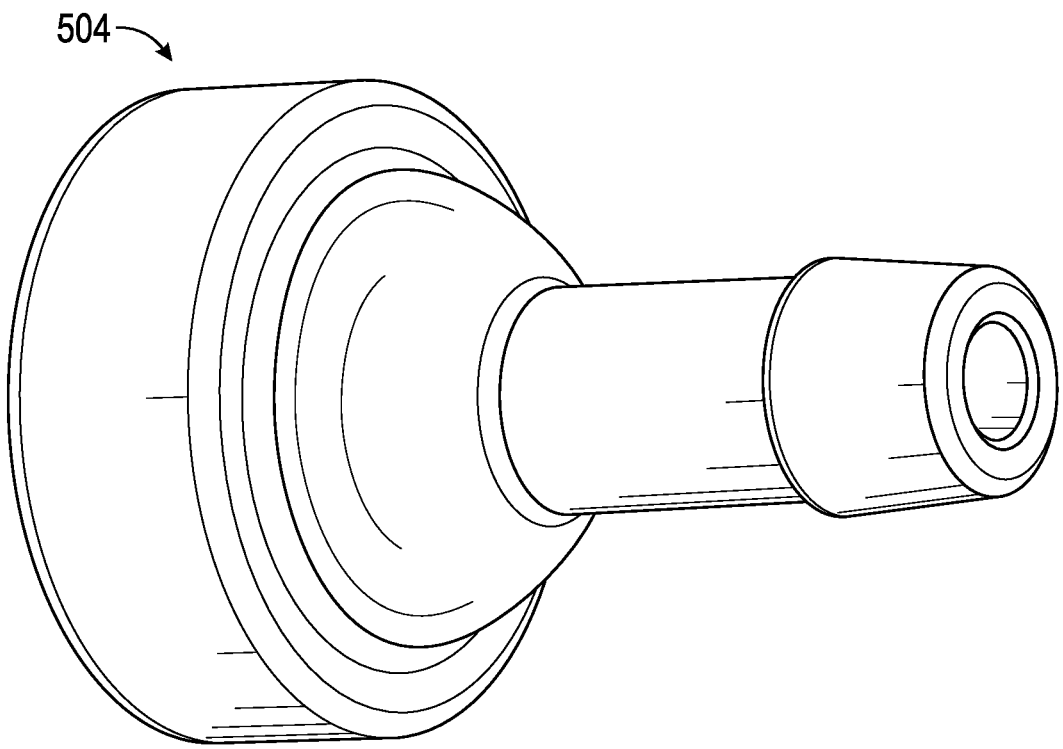
Figure 33:
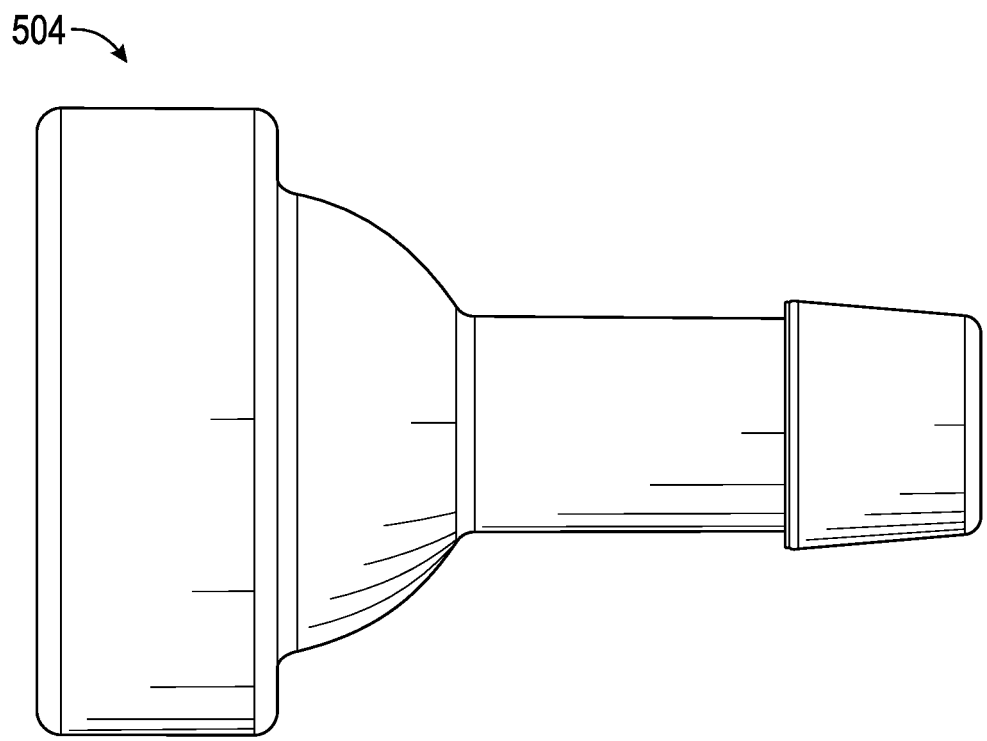
Figure 34:
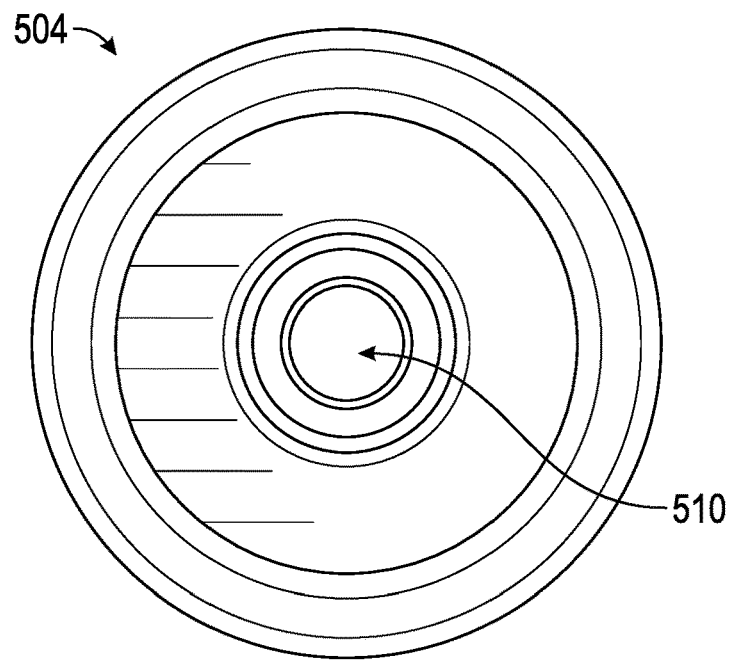
Figure 35:
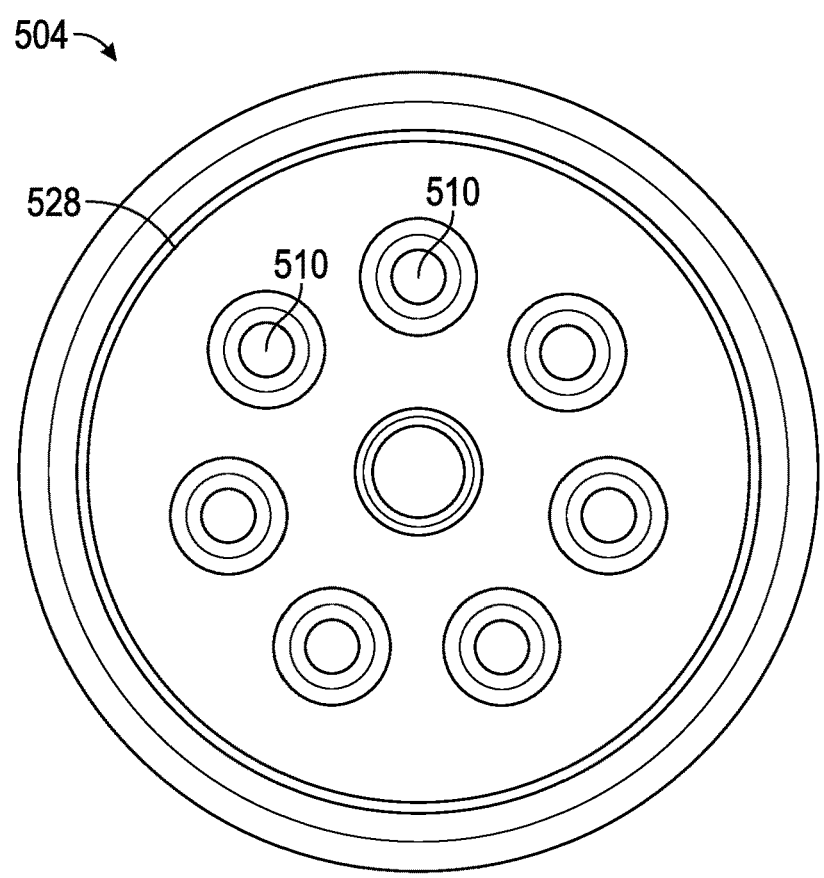

Junctions according to the various embodiments discussed above, particularly junctions 104, 204, 404 are shown in the cross sections of FIGS. 2, 10 and 23, as being substantially solid. By utilizing an additive manufacturing technique, however, the junctions (e.g. 104, 204, 404) can be created with one or more hollow cavities 450 (FIG. 30) independent of, i.e. not in fluid communication with, the plurality of fluid pathways 410. The inventors have determined that additive manufacturing provides an opportunity to build the walls of the fluid pathways 410 and the shell 454 of the junction 404 without necessarily filling in the remainder of the shell 454 with material. By creating one or more hollow cavities 450 within the junction 404, the cost of manufacturing the junction can be reduced because material costs are reduced as the volume of material used is reduced. Also, depositing less material leads to faster build times. Again, reducing the cost of manufacturing the junction.

Figure 36:
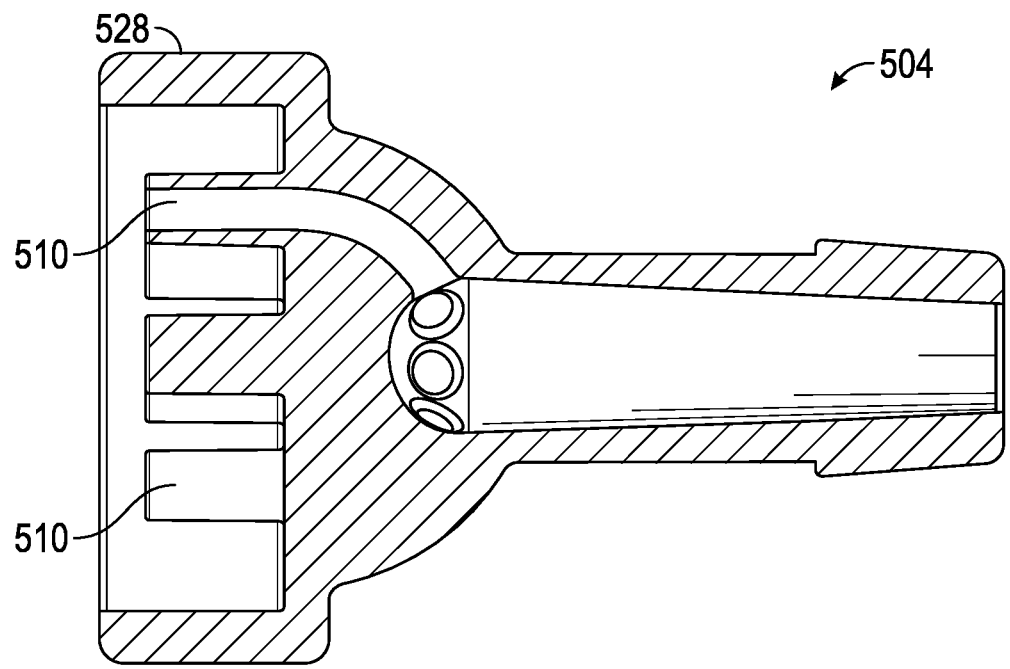
Figure 37:
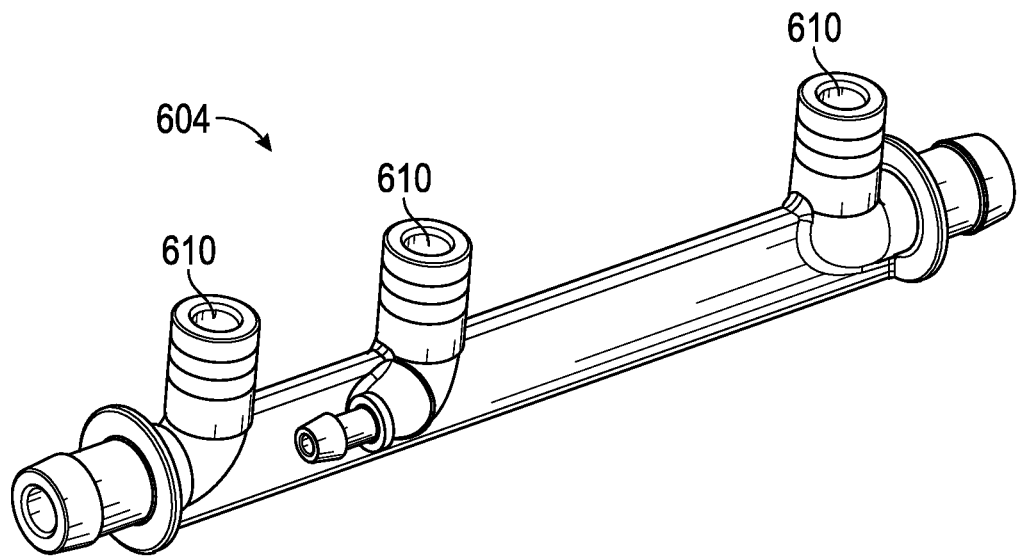
Figure 38:
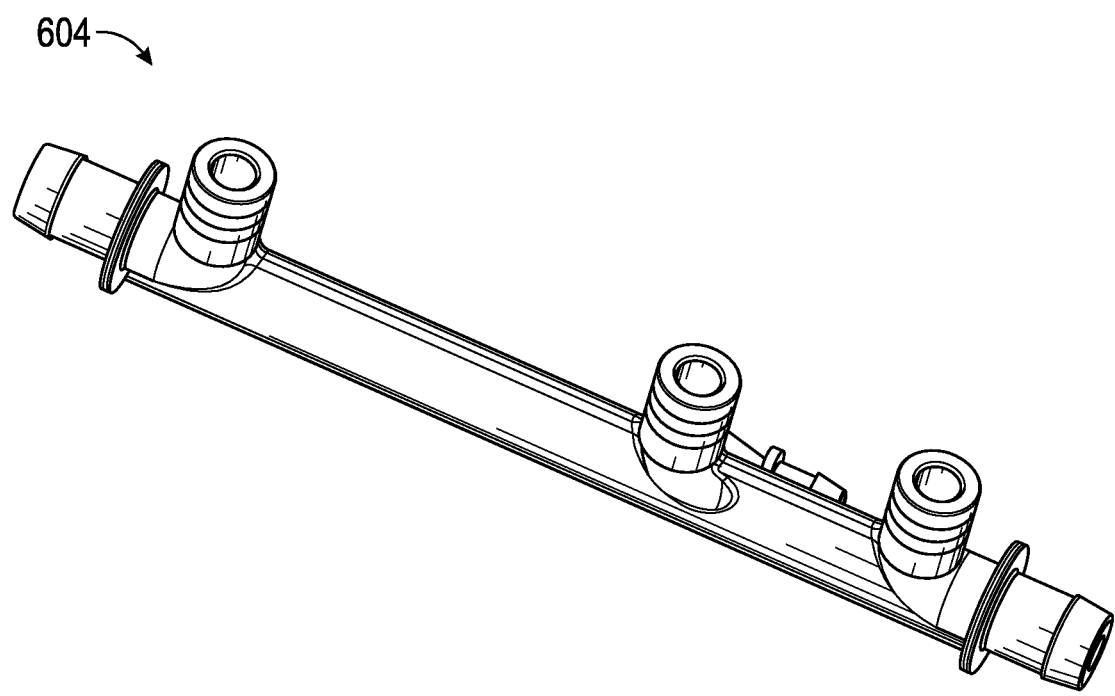
Figure 41:
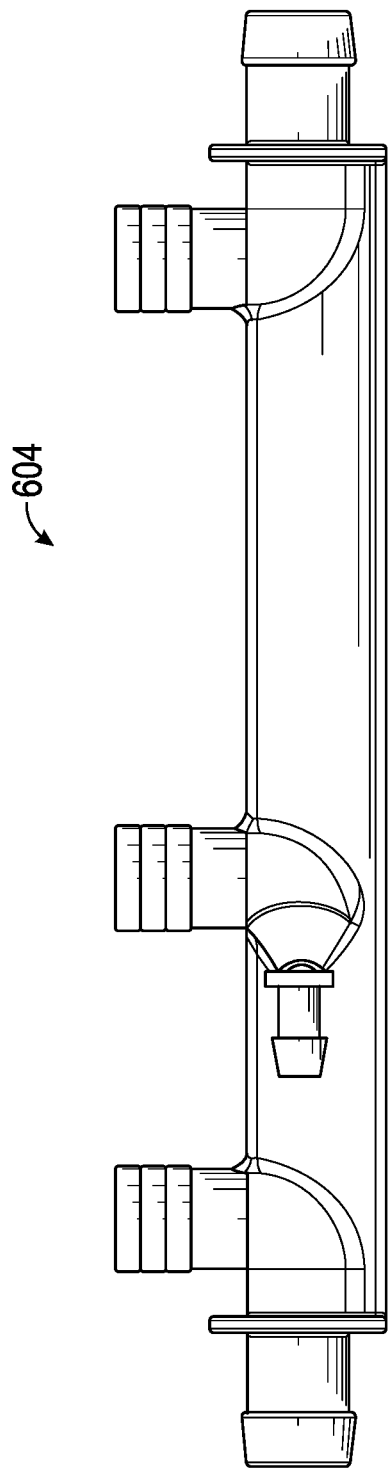
Figure 42:
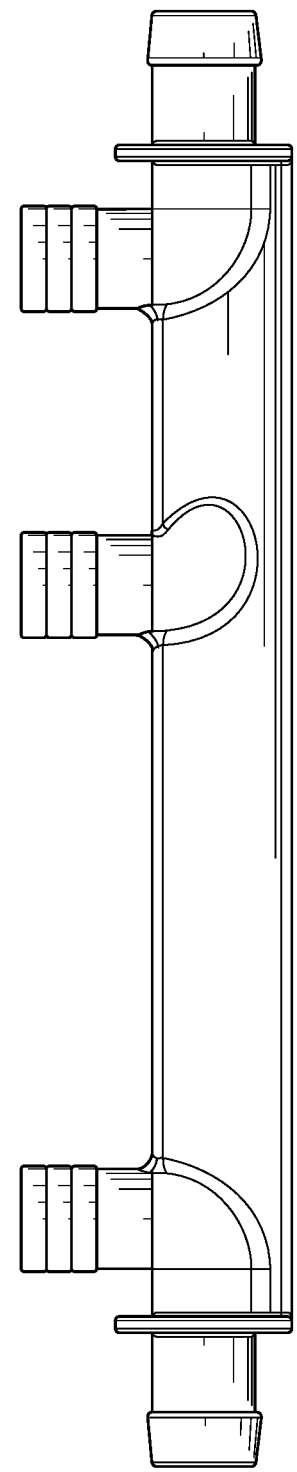
Figure 43:
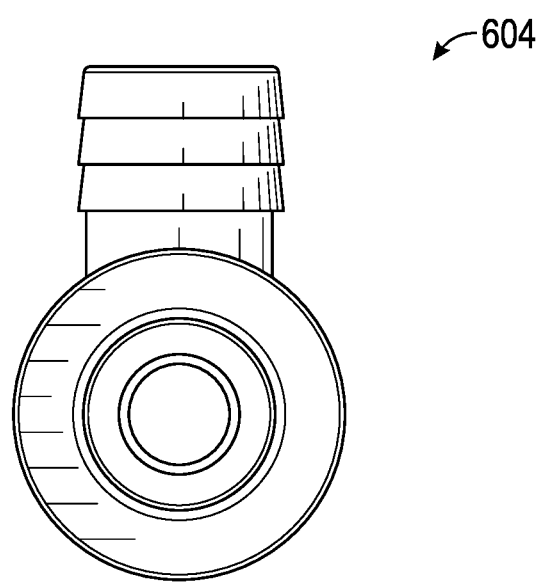

FIGS. 31-36 illustrate a junction 504 according to a fifth embodiment. The junction 504 includes a generally circular peripheral wall 528 instead of a scalloped one, but is otherwise substantially similar to the junction 104 of the first embodiment (FIGS. 1-7). FIG. 36 shows the junction 504 as substantially solid in areas other than the fluid pathways 510. In other embodiments, a hollow cavity may be integrated into the junction 504.

FIGS. 37-43 illustrate a junction 604 according to a sixth embodiment. The junction 604 may be particularly suited for attachment adjacent to or directly onto openings in a flexible polymeric container, such as a bioreactor bag. The junction 604 of the illustrated embodiment integrates three fluid pathways 610 in a fixed orientation to help maintain conduits in an organized manner. Packaging space can be reduced and the number of junctions minimized when a reducer is provided out of plane of the fluid pathways at the distal ends of the junction 604.

FIGS. 44-47 illustrate perspective and cross sectional views of a junction 704 according to a seventh embodiment. As shown in FIGS. 44-47, the junction 704 generally includes a body 705 having an upstream portion 706 and a downstream portion 708 (e.g., fluid may flow from left to right across FIG. 46); however, the junction 704 also is capable of use with the fluid flowing in the opposite direction, and thus, the terms upstream and downstream as applied to the portions 706, 708 are used solely as one example, and may be reversed.

Figure 45:
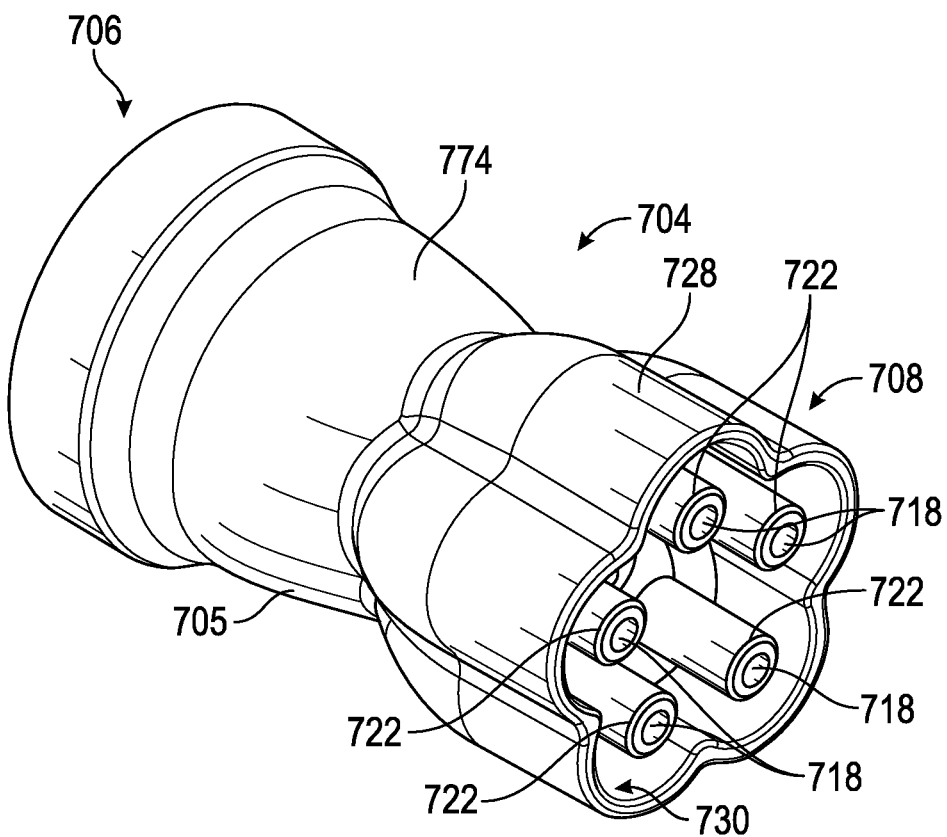
Figure 46:
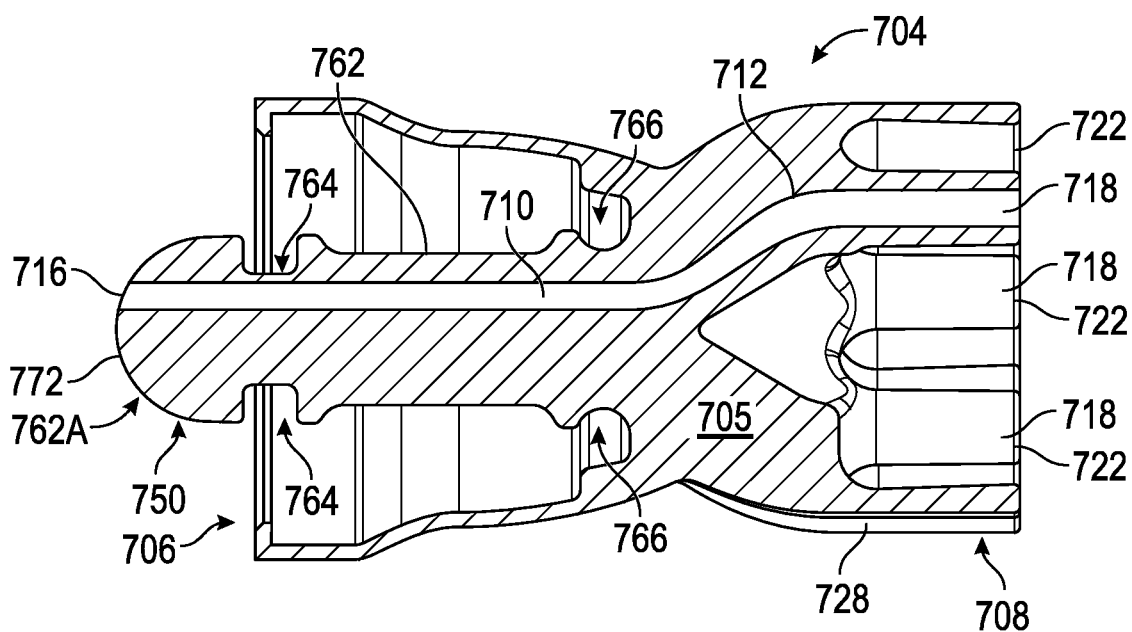

The junction 704 further includes a plurality of fluid pathways 710 defined through the junction body 705 between the upstream portion 706 and the downstream portion 708, with each fluid pathway 710 generally including at least one curved segment 712 (FIG. 46). In the illustrated embodiment, the junction 704 of FIGS. 44-46 includes five fluid pathways 710, though any suitable number of fluid pathways (e.g., less than five, such as three or four fluid pathways, or more than five, such as six, seven, eight, or more fluid pathways) can be used without departing from the scope of the present disclosure.

Figure 44:
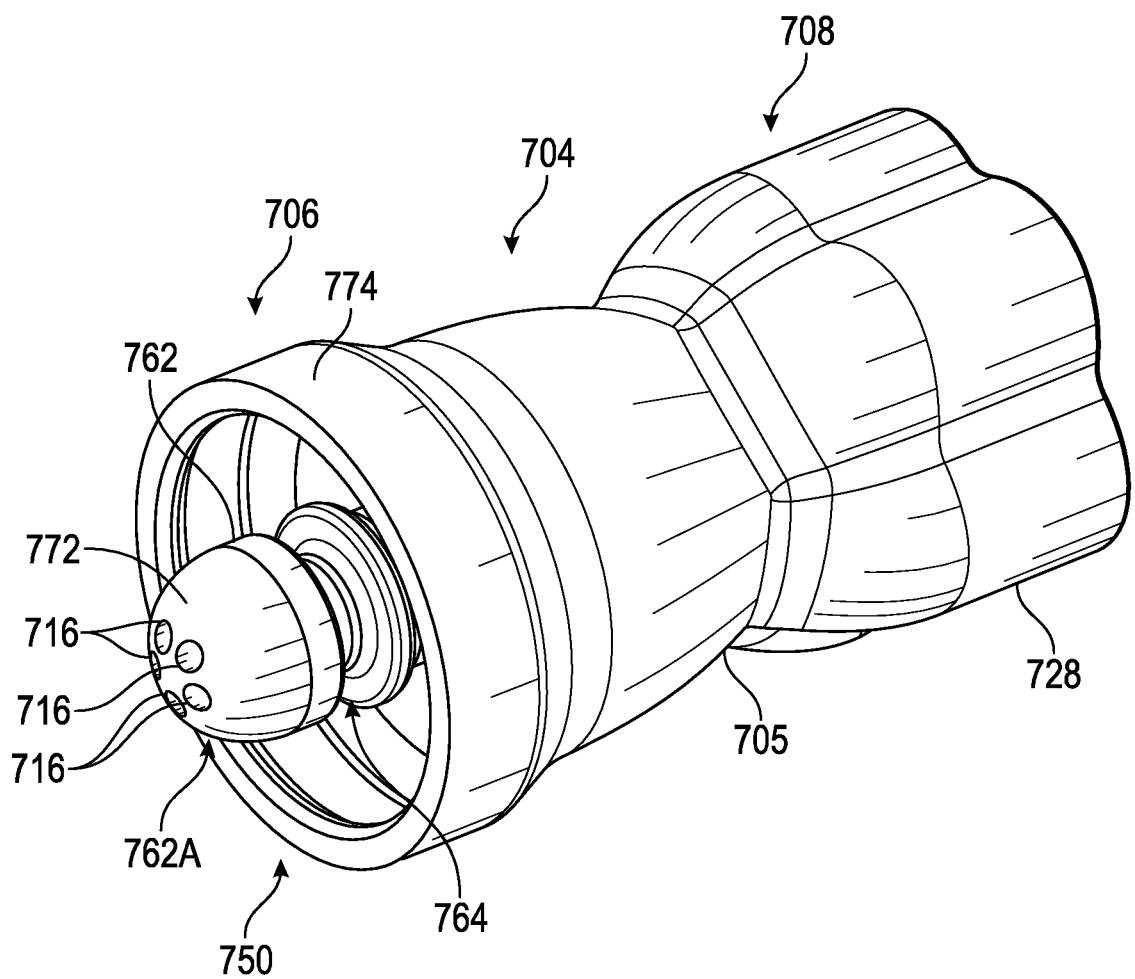
FIGS. 44, 45, 46, and 47 show perspective and cross-sectional views of a junction according to a further embodiment of the present disclosure.

The junction 704 of FIGS. 44-46 also includes five apertures 716 on the upstream portion 706 and five apertures 718 on the downstream portion 708 corresponding to the five fluid pathways 710. Each fluid pathway 710 extends between corresponding aperture 716 on the upstream portion 706 and a corresponding aperture 718 on the downstream portion 708 to place the apertures 716/718 in fluid communication with each other (e.g., to allow fluid flow into the aperture 716 and out from the aperture 718 or to allow fluid flow into the aperture 718 and out from the aperture 716).

Figure 47:
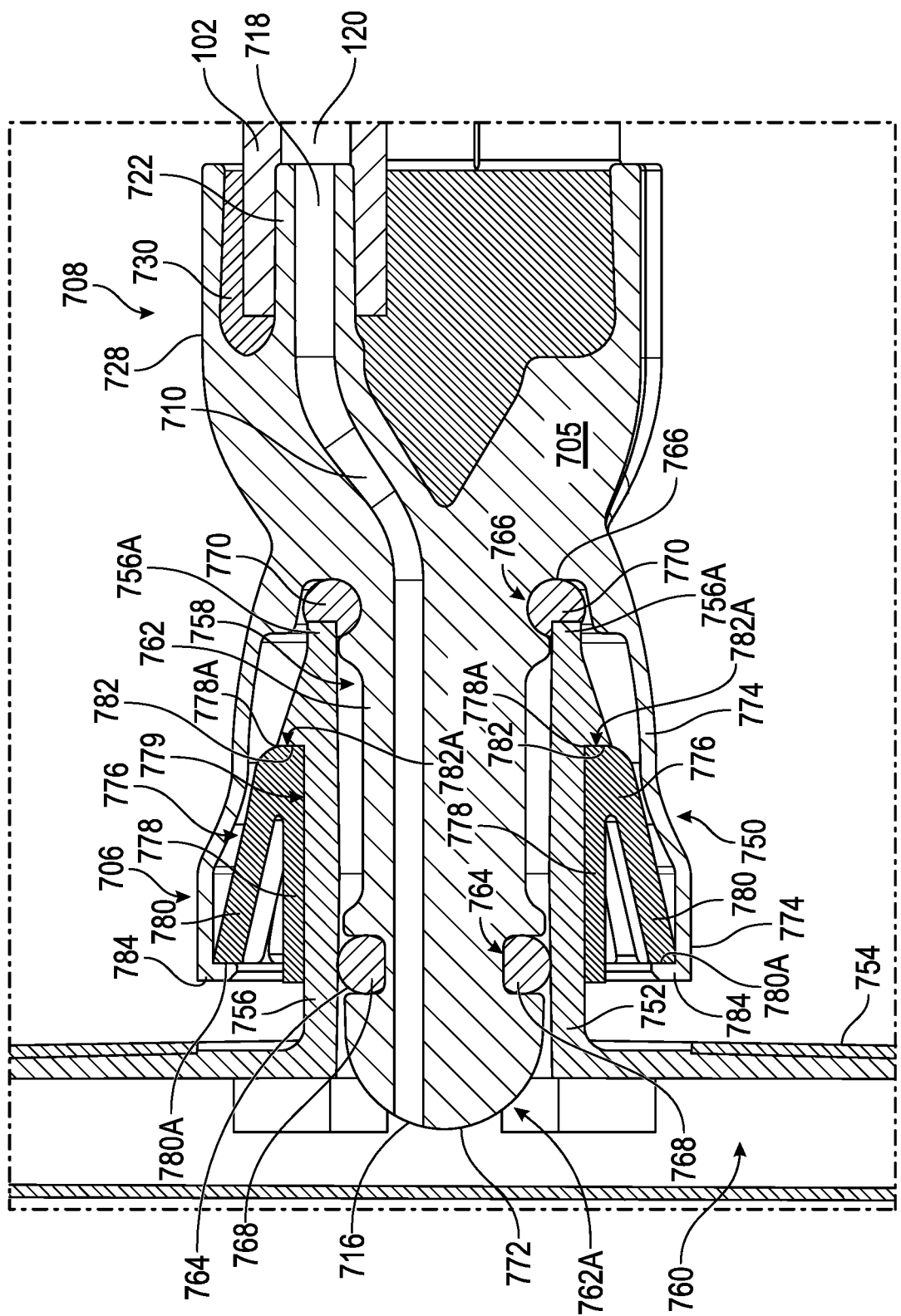

As shown in FIGS. 45, 46, and 47 the downstream portion 708 of the junction 704 additionally includes a plurality of male inserts 722 configured to attach or couple to a fluid conduit 102 to place one or more lumens 120 of the fluid conduit 102 in fluid communication with a respective fluid pathway 710. For example, the male inserts 722 each include at least a portion of the fluid pathway and include an aperture 718 defined therein. The male inserts 722 are configured to be inserted into a respective lumen 120, and generally include cylindrical tubular structures, though other suitable shapes, configurations, etc. are possible without departing from the scope of the present disclosure. The plurality of male inserts 722 further can be substantially parallel with one another. Although male inserts 722 are shown in the embodiment illustrated in FIGS. 44-47, other suitable attachment assemblies, such as female attachments or connectors (e.g., that at least partially surround and engage an exterior of the fluid conduits 102), for fluidly coupling the fluid conduits 102 to the fluid pathways 710 can be used without departing from the scope of the present disclosure.

The plurality of male inserts 722 on the downstream portion 708 of the junction 704 are surrounded by a peripheral wall 728, which also may be referred to as a flange or skirt. The peripheral wall 728 creates a cavity 730 comprised of the interstitial space between the male inserts 722. In one embodiment, the peripheral wall 728 is scalloped to generally follow the outline of a plurality of fluid conduits 102 attached to the corresponding portion of the junction 704. The plurality of fluid conduits 102 may engage at least a portion to the peripheral wall 728 when connected to the male inserts 722, e.g., to facilitate a fitted connection between the conduits and the junction, though the fluid conduits 102 may be spaced apart from (i.e., will not engage) the peripheral wall 728 when connected to the male inserts 722.

FIGS. 44-47 further show that the upstream portion 706 of the junction 704 includes a connection assembly 750 for connecting the junction 704 to a barbed connector 752 of a fluid containing vessel 754 (e.g., a fluid containing vessel including a flexible container, such as a bag, a rigid container, or other suitable vessel for receiving and storing a fluid). The barbed connector 752 can include a cylindrical body 756 defining a lumen or fluid pathway 758 that is in communication with a chamber 760 of the fluid containing vessel 754. The connection assembly 750 further includes a stem or post 762 (e.g., having a substantially cylindrical structure though other structures are possible) that is configured to be received within the lumen 758 of the barbed connector body 756, as generally shown in FIG. 47.

The stem or post 762 further includes a plurality of O-ring seats 764/766 defined therealong (FIGS. 44, 46, and 47). The O-ring seats 764/766 are configured to receive an O-ring or other suitable sealing members, such as a first O-ring 768 and a second O-ring 770 (FIG. 47). With the stem 762 received within the lumen 758 of the barbed connector body 756, the first O-ring 768 engages the interior of the lumen 758 generating a primary seal between (e.g., substantially sealing) the barbed connector 752 and the junction 704. In addition, with the stem 762 received within the lumen 758, the second O-ring 770 engages an end portion 756A of the barbed connector body 756 to create an additional or secondary seal between the barbed connector 752 and the junction 704. The secondary seal formed by the second O-ring 770 may help to maintain substantial sealing between the barbed connector 752 and the junction 704, e.g., upon failure, leakage, etc. of the first O-ring 768.

Figure 49:
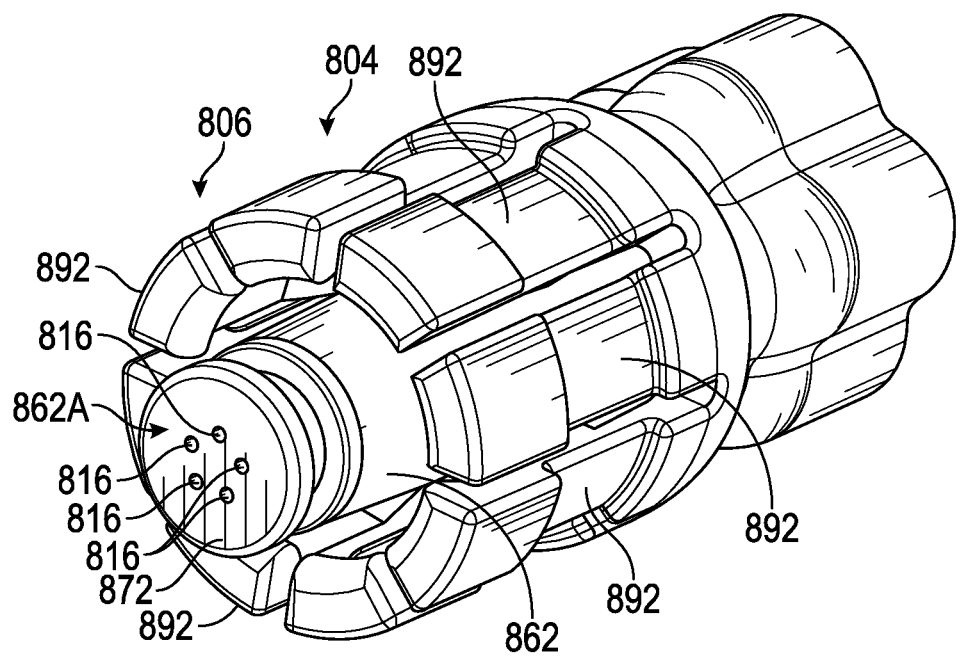
FIGS. 49, 50, 51, and 52 show perspective and cross-sectional views of a junction according to an even further embodiment of the present disclosure.
Figure 50:
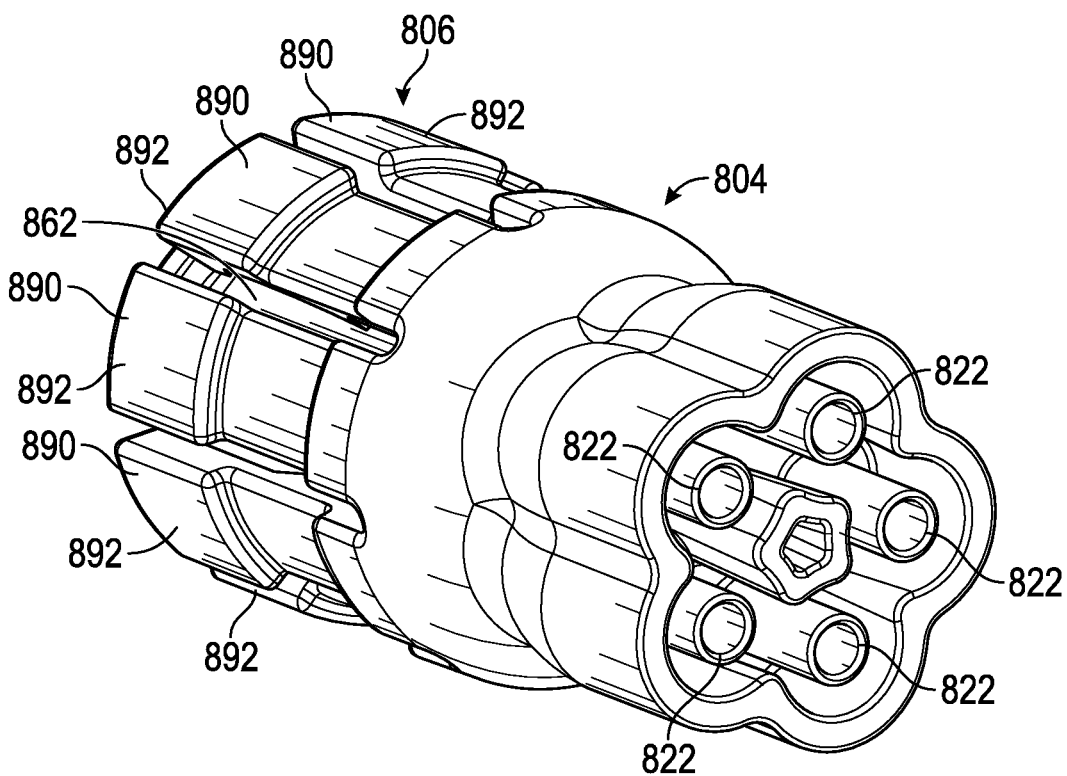
Figure 51:
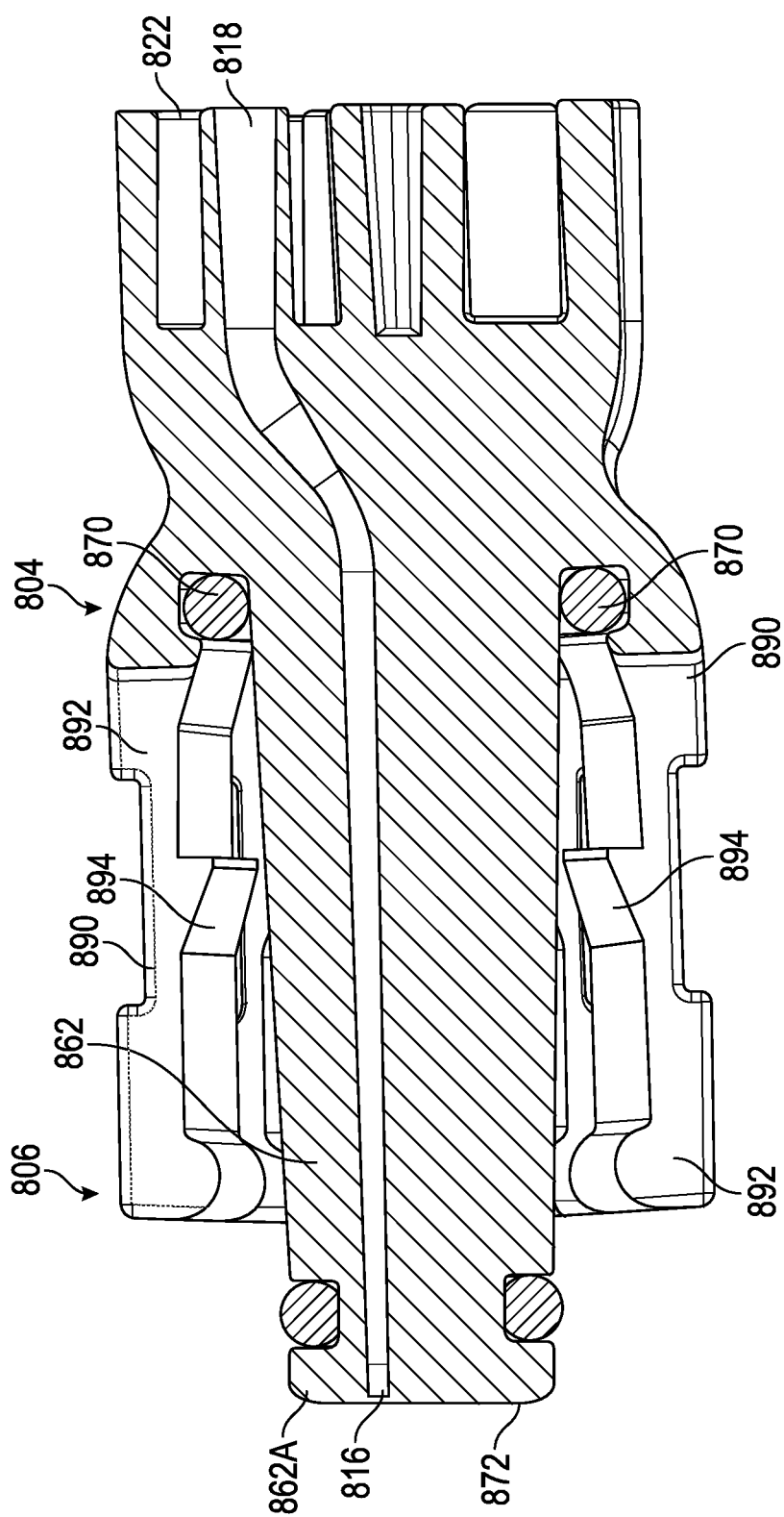
Figure 52:
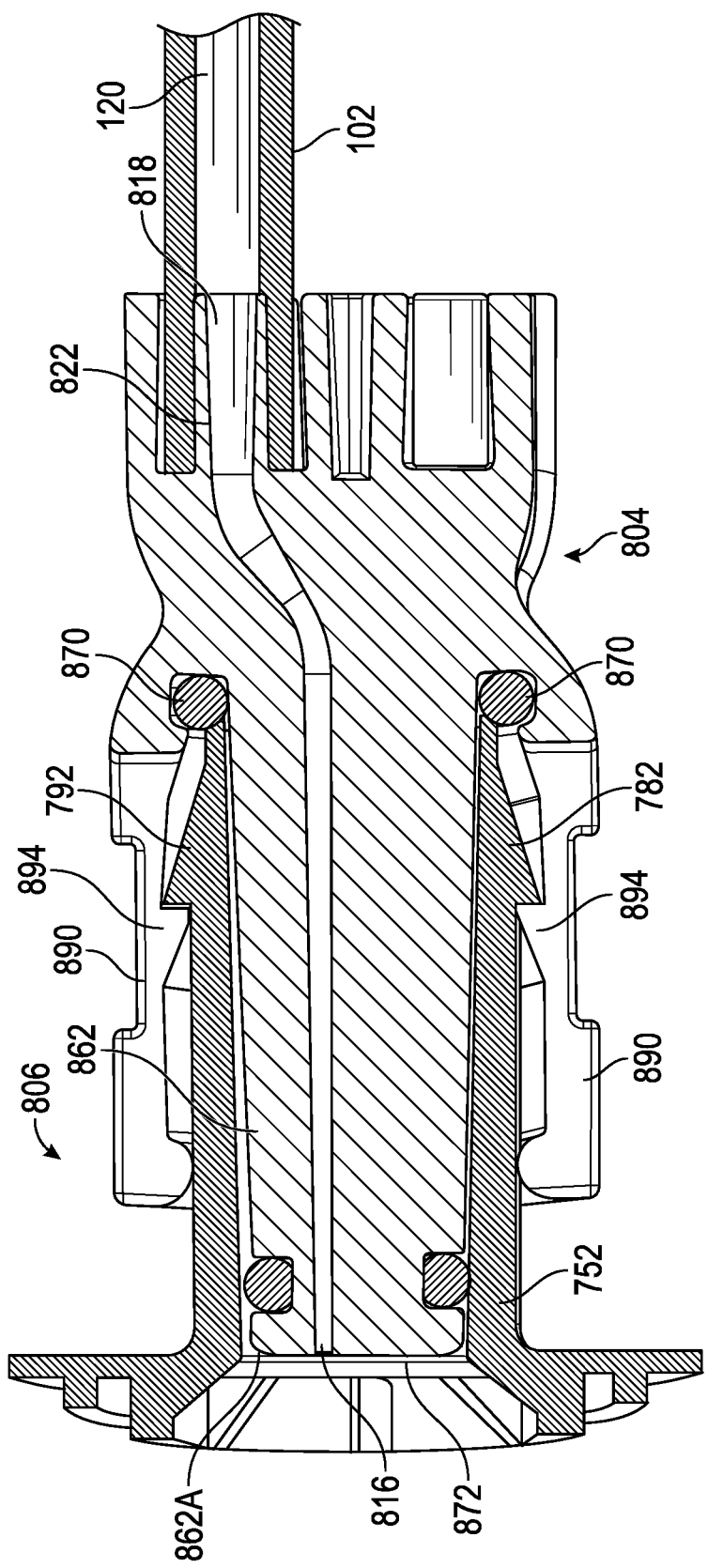

Additionally, as generally shown in FIGS. 44, 46, and 47, at least a portion of the flow pathways 710 are defined through the stem 762. The apertures 716 of the upstream portion 706 further are defined along an end portion 762A of the stem 762. In one embodiment, the end portion 762A of the stem 762 can have a generally domed, hemispherical, or arched structure, and the apertures 716 can be formed along a curved exterior surface or face 772 thereof. However, the end portion 762A of the stem 762 can have any suitable shape, structure, configuration, etc. (e.g., a substantially flat end 862A as shown in FIGS. 49, 51, and 52), without departing from the scope of the present disclosure.

Figure 48:
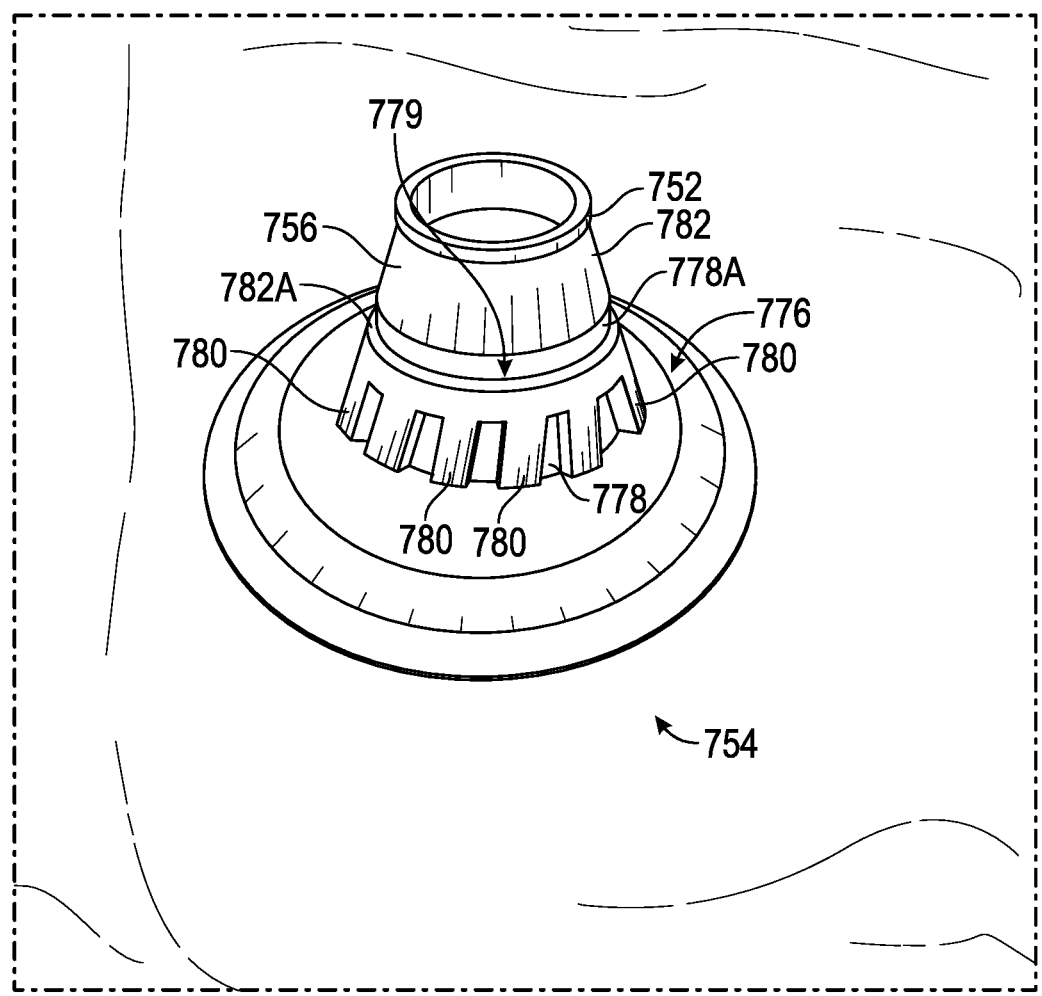
FIG. 48 shows an adapter or fitting for use with the junction shown in FIGS. 44-47.

The connection assembly 750 further includes a peripheral wall 774, which can also be referred to as a flange or skirt, that surrounds the stem 762 and is configured to facilitate connection between the junction 704 and the barbed connector 752. In one embodiment, as shown in FIGS. 47 and 48, the connection assembly 750 includes a fitting or adapter 776 that engages the peripheral wall 774 and the barbed connector body 756 to facilitate attachment/connection between the junction 704 and the barbed connector 752. The fitting 776 includes a body 778 (e.g., having a generally cylindrical structure) and a plurality of locking features 780 (e.g., projection portions or other suitable members/bodies having a generally cylindrical structure) extending from the fitting body 778. The fitting body 778 further has a passage 779 defined therethrough that is sized, shaped, configured, etc. to receive at least a portion of the barbed connector body 756. Accordingly, the fitting 776 can be received about the barbed connector body 756 such that an end portion 778A of the fitting body 778 engages a surface or face 782A defined by a barb 782 of the barbed connector 752. The peripheral wall 774 further can be received about the fitting 776 and the barbed connector 752 such that at least a portion of the locking features 780 (e.g., end portion 780A) engage a lip or shoulder 784 defined along the peripheral wall 774 to press the or engage the second O-ring 770 against the end portion 756A of the barbed connector body 756.

FIGS. 49-52 show perspective and cross sectional views of a junction 804 according to an eighth embodiment. The junction 804 is substantially similar to the junction 704 shown in FIGS. 44-47, except that the end portion 862A of the stem 862 is generally flat (e.g., with the apertures 816 being arranged on a generally flat surface 872), and the peripheral wall 774 and the fitting 776 are omitted. As shown in FIGS. 49-52, the upstream portion 806 of the junction 804 instead includes a plurality of locking features 890 configured to facilitate attachment between the barbed connector 752 and the junction 804. The locking features 890 can include a plurality of spaced apart portions or bodies 892 that have a tab, protuberance, etc. 894 defined therealong and configured to engage the barb 782 of the barbed connector 752. For example, the locking features 890 can be biased inwardly to engage the tab 894 against the barb 782 and/or to engage the tab 894 the barbed connector body 756. Accordingly, to attach/couple the junction 804 to the barbed connector 752, the locking features 890 can be received about the barbed connector body 756 until the tab 894 and the barb 782 lock into place pressing or engaging the O-ring 870 against the end portion 756A of the barbed connector body 756.

Figure 53:
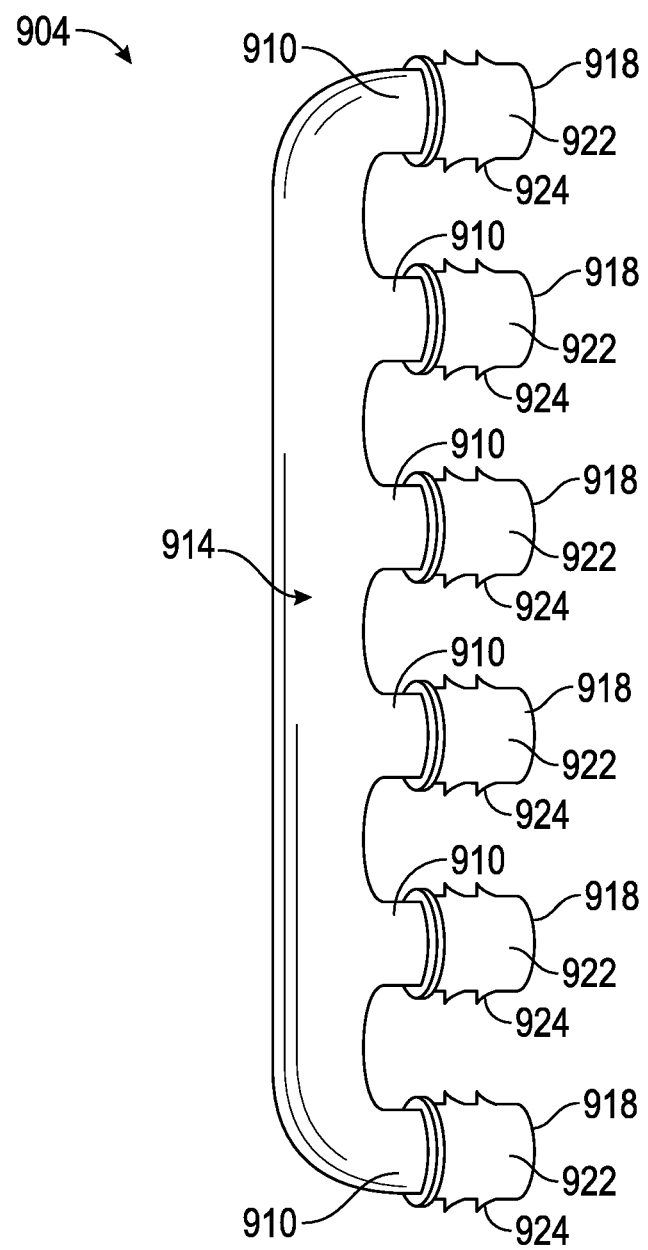
FIG. 53 illustrate a side view of a junction according to another embodiment of the present disclosure.

FIG. 53 illustrates a side view of a junction 904 according to a ninth embodiment of the present disclosure. As shown in FIG. 53, the junction 904 can include a plurality of fluid pathways 910 that are in communication with a common fluid pathway 914. In the illustrated embodiment, the junction 904 can include six fluid pathways 910 in communication with the common fluid pathway 914, though any suitable number of fluid pathways, such as two, three four, five, seven, eight, or more fluid pathways can be used without departing from the scope of the present disclosure. A set of the fluid pathways 910 can include a curved segment or portion 912. A curved segment is one that deviates from a straight line without sharp breaks or angularity. For example, the fluid pathways at the ends of the junction 904 can include a curved segment or portion 912. Another set of the fluid pathways 910 can be substantially straight (i.e., without curved segments or portions). For example, the fluid pathways 910 in between the fluid pathways 910 on the ends of the junction 904 can be substantially straight, e.g., without curved segments or portions, though fluid pathways between the ends of the fluid pathways on the ends of the junction 904 can include one or more curved segments.

FIG. 53 further shows that the junction 904 includes a plurality of male inserts 922 configured to be attached or coupled to a fluid conduit 102 to place one or more lumens 120 of the fluid conduit 102 in fluid communication with a respective fluid pathway 910. For example, the male inserts 922 each include at least a portion of the fluid pathway 910 and include an aperture 918 defined therein. The male inserts 922 are configured to be inserted into a respective lumen 120, and generally include cylindrical tubular structures. In the illustrated embodiment, the plurality of male inserts 922 are substantially parallel with one another. The male insert 922 further may be provided with one or more barbs or teeth 924 to facilitate connection/attachment to the fluid conduits 102. Though male inserts 922 are shown in the illustrated embodiment, other suitable attachment assemblies, such as female attachments or connectors (e.g., that at least partially surround and engage an exterior of the fluid conduits 102), for fluidly coupling the fluid conduits 102 to the fluid pathways 910 can be used without departing from the scope of the present disclosure.

Figure 54:
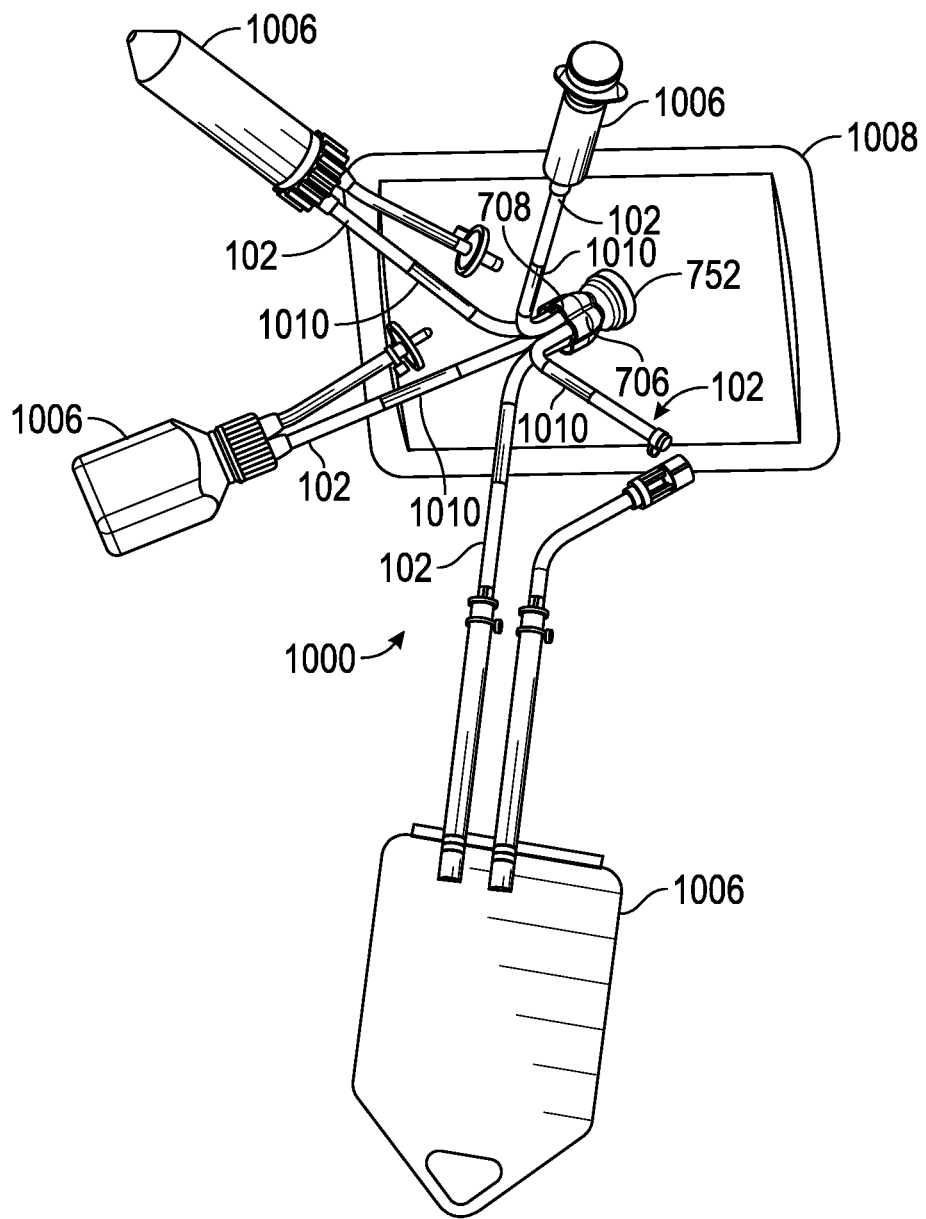
FIG. 54 illustrates a fluid transfer assembly according to one aspect of the present disclosure.

FIG. 54 shows an aseptic fluid transfer assembly 1000 according to one aspect of the present disclosure. The fluid transfer assembly 1000 includes a number of fluid conduits 102 attached to a junction (e.g., junction 704 as shown in FIGS. 44-47, though other suitable junctions as described herein, e.g., junction 804 as shown in FIGS. 49-52), may be used without departing from the scope of the present disclosure. The fluid conduits 102 are attached the downstream portion 708 of the junction 704. The fluid conduits 102 may be attached to and lead from or to one or more vessels 1006 including but not limited to containers, beakers, bottles, canisters, flasks, bags, receptacles, tanks, vats, vials, tubes, syringes, carboys, tanks, pipes, etc. that are generally used to contain liquids, slurries, and other similar substances. Additionally, the upstream portion 706 of the junction 704 can be couple to a barbed connector 752 of an additional vessel 1008. In one embodiment, the additional vessel 1008 can include a bag or other suitable, flexible container for containing liquids, slurries, and other similar substances, though the additional vessel 1008 can include rigid containers, such as bottles, flasks, beakers, or other rigid containers, without departing from the scope of the present disclosure. The barbed connector 752 can be fixed to the additional vessel 1008 by heat sealing or other suitable attachment method. The additional vessel 1008 generally has a volume that is substantially larger than the volume one or more of the vessels 1006, though the vessel 1008 can have a volume that is smaller than one or more of the vessels 1006, without departing from the scope of the present disclosure. The one or more vessels 1006 (or the vessel 1008) further can include one or more valves in communications therewith that can be activated, e.g., opened or closed, to initiate fluid transfer to and from the vessels 1006 (or the vessel 1008). For example, fluid flow may be initiated (e.g., upon opening a valve) due to pressure differentials between the vessels 1006 and the vessel 1008 (e.g., caused by a difference in volume between vessels (1006/1008)). The vessels 1006 further can include syringes or other mechanisms to draw fluid from vessel 1008.

Accordingly, with the aseptic fluid transfer assembly 1000 shown in FIG. 54, liquids, slurries, and other similar substances (e.g., provided to the vessel 1008 or the one or more vessels 1006) can be transferred between the one or more vessels 1006 and the vessel 1008 through the junction 704. In one embodiment, fluid from the vessel 1008 can flow into the apertures 716 of the upstream portion 706 of the junction 704, through the fluid pathways 710, and to the apertures 718 of the downstream portion 708 of the junction 704. Then, the fluid can flow out from the apertures 718 of the downstream portion 708 into the fluid conduits 102 and through the fluid conduits 102 into the one or more vessels 1006. For example, fluid samples can be transferred from the vessel 1008 to the one or more vessels 1006 for sterility testing, cell viability testing, or other suitable testing of biologic samples.

In addition, or in alternative embodiments, fluids can be transferred from the one or more vessels 1006 to the vessel 1008 (e.g., an acid or a base may be provided to the vessel 1008 from one or more of the vessels 1006, an antifoam agent can be provided from one or more of the vessels 1006 to the vessel 1008 to reducing foaming therein, small packages of cells can be provided from one or more of the vessels 1006 to the vessel 1008 to facilitate cell growth therein, or other suitable fluids can be provided or otherwise introduced from the one or more vessels 1006 to the vessel 1006, such as to inoculate the vessel 1008). For example, the fluid flows from the one or more vessels 1006 into the fluid conduits 102 and from the fluid conduits 102 into the apertures 718 of the downstream portion 708 of the junction 704. Thereafter, the fluid flows through the fluid pathway 710 in the junction 704 to the apertures 716 in the upstream portion 706 of the junction 704, and out from the apertures 716 and into the vessel 1008.

Turning again to the embodiment shown in FIGS. 44-47, the apertures 716 at the upstream portion 706 of the junction 704 can have a diameter that is substantially smaller than the diameter of the apertures 718 at the upstream portion 708 of the junction 704. For example, apertures 716 can have a diameter in the range of about 0.05 mm to about 5.0 mm, such as about 0.06 mm, about 0.07 mm, about 0.08 mm, about 0.1 mm, about 0.12 mm, about 0.13 mm, about 0.14 mm, about 0.15 mm, about 0.16 mm, about 0.17 mm, about 0.18 mm, about 0.19 mm, about 0.2 mm, about 0.3 mm, about 0.4 mm, about 0.5 mm, about 0.6 mm, about 0.7 mm, about 0.8 mm, about, 0.9 mm, about 1.0 mm, about 2.0 mm, about 3.0 mm, about 4.0 mm, or other suitable numbers therebetween, though diameters less than 0.05 mm and greater than 5 mm can be used without departing from the scope of the present disclosure. On the other hand, the apertures 718 can have a diameter in the range of about 5 mm to about 20 mm, such as about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, or other suitable numbers therebetween, though the diameters less than 5 mm and greater than 20 mm can be used without departing from the scope of the present disclosure. The apertures 716 are generally sized, dimensioned, configured, etc. such that liquids, slurries, and other similar substances of suitable viscosities can flow into and out from the apertures 716 through the junction 704, and further the apertures 716 can be generally sized, dimensioned, configured, etc. to help to substantially prevent, reduce, or inhibit back or return flow from the fluid pathways 710, e.g., back or return flow from the fluid pathway 710 when a sealable portion 1010 of the fluid conduits (FIG. 54) are clamped, crimped, or otherwise closed to seal of the conduits or other closing is applied to the conduits 102. The sealable portion can include Quickseal® portions available from Sartorius Stedim North America, and example sealable portions are shown and described in co-owned U.S. Pat. No. 8,505,586, which is incorporated by reference herein as if set forth in its entirety. The apertures 816 and 818 of the junction 804 shown in FIGS. 49 to 52 further can have similar constructions (e.g., identical constructions) to the apertures 716 and 718 of the junction 704 shown in FIGS. 44-47.

A method of manufacturing/assembling a fluid transfer assembly can include fixing the barbed connector 752 to the vessel 1008 (e.g., if the vessel 1008 includes a bag, the barbed connector 752 can be fixed thereto by heat sealing the barbed connector 752 to the bag). The method additionally can include attaching a junction according to the embodiments described herein, such as junction 704, junction 804, or other suitable junction described herein to the barbed connector 752, e.g., the upstream portion 706/806 of the junction 704/806 can be attached to the barbed connector 752 as described above. Further, the conduits 102 can be attached to the downstream portion 708/808 of the junction 704/804 as described above. For example, the method may include inserting at least one of the plurality of male inserts 722/822 into a lumen 120 of a flexible fluid conduit 102 and securing the flexible fluid conduit to the junction. The conduits 102 further can be attached to the one or more vessels 1006. Upon assembly of fluid transfer assembly (e.g., upon connection of the vessel 1008, junction 704/804, conduits 105, and one or more vessels 1006), the fluid transfer assembly can be packaged in a single polyethylene bag, multiple polyethylene bags, or other suitable packaging, such as in thermoformed trays with removable lids or other suitable containers, e.g., to form a packaged assembly. After packaging the fluid transfer assembly, the packaged assembly can be rendered substantially aseptic, e.g., by applying gamma radiation, as described below. It will be understood, however, that above steps are not limited to any particular order or sequence and one or more of the above steps can be rearranged, omitted, or additional steps added, without departing from the scope of the present disclosure. For example, the assembly can be rendered substantially aseptic prior to packaging and/or one or more of the conduits and their corresponding vessels can be attached to the junction prior to attachment of the junction and the barbed connector.

To save space and minimize the use of separate components, the junctions 104, 204, 304, 404, 504, 604, 704, 804, and 904 of the present disclosure each have at least one fluid pathway through the junction that includes a non-linear, preferably curved segment. As mentioned above, implementing the preferred route of each fluid pathway can be difficult, or simply not feasible using traditional injection molding or boring techniques.

Therefore, in some embodiments, a method of manufacturing/assembling a fluid transfer assembly according to the present disclosure may include the step of depositing sequential layers of material using an additive manufacturing device (e.g. a 3D printer) to form a unitary junction having an upstream portion and a downstream portion, the unitary junction defining a plurality of curved fluid pathways between the upstream portion and the downstream portion. Alternatively, the junction can be formed using CLIP technology, e.g., as offered by Carbon, Inc., which, e.g., uses digital light synthesis to use patterns of light to partially cure a product layer by layer with the uncured material being cured to the bottom of the stack as a body of cured or semi-cured material is lifted from the reservoir of uncured material. In some embodiments, at least one of the upstream portion and the downstream portion comprises a plurality of male inserts respectively corresponding with the plurality of fluid paths.

During the step of depositing sequential layers of material, the act of deposition of material may create at least one hollow cavity within the junction that is sealed off from the plurality of fluid pathways. The method also includes inserting the plurality of male inserts into a lumen of a flexible fluid conduit and securing the flexible fluid conduit to the junction. In one embodiment, the step of securing the flexible fluid conduit to the junction comprises over-molding the conduit to the junction.

The method of manufacturing/assembling the fluid transfer assemblies further may comprise rendering the fluid transfer assembly substantially aseptic by, for example, gamma radiation. Alternatively, the entire fluid transfer assembly, or components, thereof may be rendered substantially aseptic by exposure to steam above 121° C. for a period of time long enough to eliminate microorganisms. The entire assemblies or components thereof may also be rendered aseptic by chemical treatment, such as with ethylene oxide (ETO). Once rendered substantially aseptic, the fluid transfer assemblies may be appropriately packaged and stored to maintain the substantially aseptic state until ready for use.

The foregoing description generally illustrates and describes various embodiments of this disclosure. It will, however, be understood by those skilled in the art that various changes and modifications can be made to the above-discussed constructions and systems without departing from the spirit and scope of this disclosure as disclosed herein, and that it is intended that all matter contained in the above description or shown in the accompanying drawings shall be interpreted as being illustrative, and not to be taken in a limiting sense. Furthermore, the scope of the present disclosure shall be construed to cover various modifications, combinations, additions, alterations, etc., above and to the above-described embodiments, which shall be considered to be within the scope of this disclosure. Accordingly, various features and characteristics as discussed herein may be selectively interchanged and applied to other illustrated and non-illustrated embodiment, and numerous variations, modifications, and additions further can be made thereto without departing from the spirit and scope of the present invention as set forth in the appended claims.

The invention claimed is:

1. A fluid transfer assembly, comprising:
a unitary junction having an upstream portion and a downstream portion, the unitary junction defining a plurality of curved fluid pathways between the upstream portion and the downstream portion, each of the curved fluid pathways defining a central axis along a length thereof, the central axis comprising a linear first segment, a curved second segment, and a linear third segment, the second segment disposed between the first and third segments, the second segment of the central axis deviating from a straight line to define a smooth curve, a linear projection of the first segment intersecting a linear projection of the third segment outside of the respective curved fluid pathway or the first and third segments being parallel to one another; and
at least one flexible fluid conduit sealed to the junction in fluid communication with at least one of the plurality of curved fluid pathways,
wherein fluid is transferred from a primary vessel to a secondary vessel through the unitary junction.

2. The fluid transfer assembly of claim 1, wherein the plurality of fluid pathways from the upstream portion to the downstream portion are free from diaphragm capable of restricting or stopping flow.

3. The fluid transfer assembly of claim 1, wherein the junction comprises a hollow cavity independent of the plurality of fluid pathways.

4. The fluid transfer assembly of claim 1, further comprising at least one additional component comprising at least one of a vessel, a fitting, and a connector.

5. The fluid transfer assembly of claim 1, wherein the unitary junction is formed from a plurality of layers of material.

6. The fluid transfer assembly of claim 5, wherein of the plurality of layers is each layer being approximately the same thickness.

7. The fluid transfer assembly of claim 1, wherein:
the junction comprises a common pathway portion that provides a portion of at least two of the plurality of curved fluid pathways.

8. The fluid transfer assembly of claim 7, wherein:
the common pathway portion is arranged such that a number of apertures on the downstream portion is not equal to a number of apertures on the upstream portion.

9. The fluid transfer assembly of claim 1, wherein the upstream portion of the downstream portion includes a connector assembly for coupling the junction to a barbed connector of the supply vessel, and wherein the connector assembly includes a stem and a peripheral wall at least partially surrounding the stem for facilitating attachment of the unitary junction to the barbed connector.

10. The fluid transfer assembly of claim 9, wherein the connection assembly includes a fitting for engaging the barbed connector and the peripheral wall, wherein the fitting includes a body with a plurality of locking features extending therefrom and configured to engage at least a portion of the unitary junction.

11. The fluid transfer assembly of claim 10, wherein the unitary junction is formed by digital light synthesis using patterns of light to at least partially cure the unitary junction layer by layer with uncured material being cured to a bottom of a stack as a body of cured or semi-cured material is lifted from a reservoir of uncured material.

12. The fluid transfer assembly of claim 1, wherein at least one of the upstream portion and the downstream portion comprises a plurality of male inserts respectively corresponding with the plurality of fluid pathways, the plurality of male inserts for insertion into the at least one fluid conduit to facilitate fluid communication.

13. The fluid transfer assembly of claim 12, wherein the at least one fluid conduit comprises a plurality of lumen equal to the plurality of male inserts such that each insert engages a respective lumen of the at least one fluid conduit.

14. The fluid transfer assembly of claim 12, wherein the plurality of male inserts are substantially parallel with one another.

15. The fluid transfer assembly of claim 12, wherein the plurality of male inserts are arranged radially around a central axis of the junction.

16. The fluid transfer assembly of claim 15, wherein the junction comprises indicia adjacent to a single one of the plurality of male inserts, the indicia adjacent to the single one of the male inserts that corresponds with a fluid pathway accessible along the central axis of the junction.

17. The fluid transfer assembly of claim 12, wherein the junction comprises a peripheral wall that surrounds the plurality of male inserts.

18. The fluid transfer assembly of claim 17, wherein a curable material is contained by the peripheral wall and attaches the at least one flexible fluid conduit to the junction.

19. The fluid transfer assembly of claim 17, wherein the peripheral wall is scalloped.

20. A fluid transfer assembly, comprising:
    a unitary junction having an upstream portion and a downstream portion, the unitary junction including walls defining a plurality of curved fluid pathways between the upstream portion and the downstream portion, each of the curved fluid pathways defining a central axis, the walls defining each curved fluid pathway comprising a linear first section, a curved second section, and a linear third section disposed between the first section and the third section, the second section defining a segment of the central axis having a smooth curve along a length thereof, the second section having a length along the central axis greater than a diameter of the curved fluid pathway;
    at least one flexible fluid conduit sealed to the junction in fluid communication with at least one of the plurality of curved fluid pathways; and
    at least one vessel connected to the at least one flexible fluid conduit,
    wherein at least one of the upstream portion and the downstream portion comprises a plurality of male inserts respectively corresponding with the plurality of fluid pathways, the plurality of male inserts for insertion into the at least one fluid conduit to facilitate fluid communication.

21. The fluid transfer assembly of claim 20, wherein the at least one vessel includes a bag, beaker, bottle, canister, flask, tank, vat, vial, tube, syringe, or combinations thereof.

22. The fluid transfer assembly of claim 20, wherein the unitary junction is formed from a plurality of layers of material, each layer being approximately the same thickness.

23. The fluid transfer assembly of claim 20,
    wherein the unitary junction comprises a hollow cavity independent of the plurality of fluid pathways.

24. The fluid transfer assembly of claim 20, wherein:
    the junction comprises a common pathway portion that forms part of at least two of the plurality of curved fluid pathways,
    wherein the common pathway portion is arranged such that a number of access points on the downstream portion is not equal to a number of access points on the upstream portion.

25. The fluid transfer assembly of claim 20, wherein the junction comprises a peripheral wall that surrounds the plurality of male inserts, where in a curable material is contained by the peripheral wall and attaches the at least one flexible fluid conduit to the junction.

26. The fluid transfer assembly of claim 20, wherein the at least one flexible fluid conduit comprises a plurality of lumen equal to the plurality of male inserts such that each insert engages a respective lumen of the at least one flexible fluid conduit.

27. The fluid transfer assembly of claim 20, wherein the plurality of male inserts are substantially parallel with one another.

28. The fluid transfer assembly of claim 20, wherein the plurality of male inserts are arranged radially around a central axis of the junction.

29. The fluid transfer assembly of claim 28, wherein the junction comprises indicia adjacent to a single one of the plurality of male inserts, the indicia adjacent to the single one of the male inserts that corresponds with a fluid pathway accessible along the central axis of the junction.

30. A method of manufacturing a fluid transfer assembly, comprising:
    forming sequential layers of material using an additive manufacturing device to form a unitary junction having an upstream portion and a downstream portion, the unitary junction defining a plurality of curved fluid pathways between the upstream portion and the downstream portion, each of the curved fluid pathways defining a central axis, the central axis comprising a linear first segment, a curved second segment, and a linear third segment, the second segment disposed between the first and third segments, the second segment of the central axis deviating from a straight line to device a smooth curve, a linear projection of the first segment intersecting a projection of the third segment outside of the respective curved fluid pathway or the first and third segments being parallel to one another, wherein at least one of the upstream portion and the downstream portion comprises a plurality of male inserts respectively corresponding with the plurality of fluid pathways;
    inserting at least one of the plurality of male inserts into a lumen of a flexible fluid conduit; and
    securing the flexible fluid conduit to the junction.

31. The method of claim 30, wherein the step of depositing comprises creating a hollow cavity within the junction that is sealed off from the plurality of fluid pathways.

32. The method of claim 30, wherein the step of securing the flexible fluid conduit to the junction comprises overmolding the conduit to the junction.

33. The method of claim 30, further comprising:
    rendering the junction and the flexible fluid conduit substantially aseptic; and
    packaging the junction and the flexible fluid conduit to maintain the substantially aseptic state until ready for use.

34. The method of claim 30, further comprising treating an exterior surface of the junction.

35. A method for fluid transfer through a unitary junction, comprising:
    providing a fluid to a first vessel connected to an upstream portion of the unitary junction, the upstream portion having a connection assembly for engaging a connector of the first vessel;
    transferring the fluid through one or more curved fluid pathways of a plurality of fluid pathways defined through the unitary junction, each of the curved fluid pathways defining a central axis, the central axis comprising a linear first segment, a curved second segment, and a linear third segment, the second segment disposed between the first and third segments, the second segment of the central axis deviating from a straight line to define a smooth curve, a linear projection of the first segment intersecting a linear projection of the third segment outside of the respective curved fluid pathway or the first and third segments being parallel to one another; and receiving the fluid in a second vessel in communication with a downstream end of the unitary junction through a flexible conduit.

\* \* \* \* \*